United States Patent

Komoto et al.

Patent Number: 5,532,371
Date of Patent: Jul. 2, 1996

[54] PIPERAZINE SUBSTITUTED CARBOXYLIC ACID DERIVATIVES FOR TREATING HYPERLIPIMIA

[75] Inventors: Teruo Komoto, Chiba; Hiroyuki Hirota; Susumu Sato, both of Shisui-machi; Mari Ohtsuka, Narashino; Hidehiko Koya, Narita; Hiroyuki Mizuno, Tomisato-machi; Tadayuki Kuraishi, Narashino, all of Japan

[73] Assignee: SS Pharmaceutical Co., Ltd., Tokyo, Japan

[21] Appl. No.: 377,965

[22] Filed: Jan. 25, 1995

Related U.S. Application Data

[62] Division of Ser. No. 158,398, Nov. 29, 1993, Pat. No. 5,411,972.

[30] Foreign Application Priority Data

Dec. 8, 1992 [JP] Japan ................ 4-328164
Jun. 7, 1993 [JP] Japan ................ 5-136119

[51] Int. Cl.$^6$ .................... C07D 401/10
[52] U.S. Cl. .......... 544/360; 544/363; 544/379; 544/392; 544/394
[58] Field of Search .............. 544/363, 360, 544/379, 392, 394

[56] References Cited

U.S. PATENT DOCUMENTS 4,616,086 10/1986 Witte et al. ............... 544/383

OTHER PUBLICATIONS

Stuetz et al. "Preparation ofazolylpneylethyamides as medical and agrochemical fungicides" CA 108:21901 (1987).

Primary Examiner—Ceila Chang
Attorney, Agent, or Firm—Oblon, Spivak, McClelland, Maier & Neustadt

[57] ABSTRACT

An arylamide derivative of formula (1), a salt thereof and a therapeutic agent for hyperlipemia which comprises the derivative or salt:

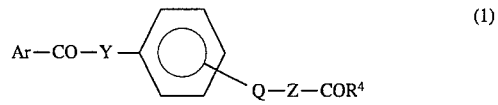

(1)

wherein Ar represents a group

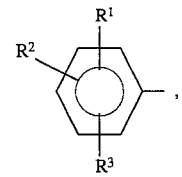

a naphthyl group, a pyridinyl group, a furyl group, a thienyl group, a quinolyl group or an indolyl group; Y represents a group

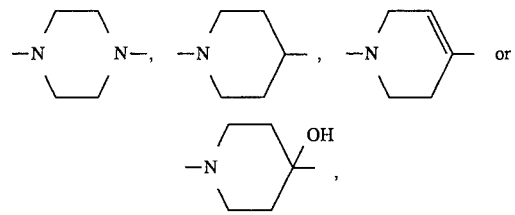

and Q represents —O— or a single bond, Z represents an alkylene group, and $R^4$ represents a hydroxyl group, an alkoxy group or a group —NH(CH$_2$)$_m$COOH.

2 Claims, No Drawings

PIPERAZINE SUBSTITUTED CARBOXYLIC ACID DERIVATIVES FOR TREATING HYPERLIPIMIA

This is a Division of application Ser. No. 08/158,398 filed on Nov. 29, 1993 now U.S. Pat. No. 5,411,972.

BACKGROUND OF THE INVENTION

1. Field of the Invention

The present invention relates to novel arylamide derivatives and salts thereof, and therapeutic agents for hyperlipemia containing the derivatives or salts which exhibit excellent anti-hyperlipemic action.

2. Description of the Related Art

Conventionally, there are many drugs known as therapeutic agents for hyperlipemia. Upon clinical use of a drug for the treatment of hyperlipemia, profile of the disease and functional mechanism of the drug must be taken into account for properly select a drug which is suited for the purpose of treatment. Generally speaking, the purpose of administering the drug is to lower the level of total serum cholesterol (TC), lower the level of triglyceride (TG), or to lower the levels of both, and drugs are selected accordingly.

Recently, the dangerousness of hypertriglyceridemia is highlighted as a risk factor of arteriosclerosis, coronary diseases, cerebrovascular disorders, obesity and the like diseases which involve hyperlipemia, and from the viewpoint of the prevention and treatment of diseases associated with hyperlipemia, the importance of lowering the level of triglyceride in blood has now been recognized.

Conventionally, clofibrate-type drugs have been developed to lower the level of triglyceride in blood, and clofibrate, clinofibrate, phenofibrate, bezafibrate and the like are clinically used.

However, these clofibrate-type drugs are accompanied by adverse side effects such as gastroenteric disorders and liver disorders, and moreover, they must be administered in a large quantity for obtaining a certain clinical effect, and the effect is still unsatisfactory.

Accordingly, therapeutic agents for hyperlipemia which exhibit excellent anti-hyperlipemic action and are very safe have still been desired.

Under the above-mentioned circumstances, the inventors of the present invention have synthesized many arylamide derivatives and carried out extensive studies on their anti-hyperlipemic action, and have found that the arylamide derivatives represented by the formula (1) which will be described hereinbelow or salts thereof have excellent action of lowering the level of cholesterol in blood, lowering the level of triglyceride in blood, are very safe and are useful as a therapeutic agent for hyperlipemia associated with arteriosclerosis, myocardial infarction, high blood pressure and cerebrovascular disorders, leading to completion of the present invention.

SUMMARY OF THE INVENTION

Accordingly, an object of the present invention is to provide an arylamide derivative represented by formula (1) and salts thereof:

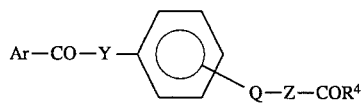
(1)

wherein Ar represents a group

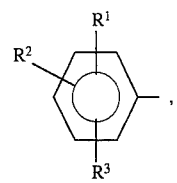

in which $R^1$, $R^2$ and $R^3$ are the same or different from each other and each independently represents a hydrogen atom, a halogen atom, a hydroxyl group, an alkyl group which may be substituted by a halogen atom, an alkoxy group, an alkenyl group, an acylamino group or a carboxyalkyloxy group,
a naphthyl group, a pyridinyl group, a furyl group, a thienyl group, a quinolyl group or an indolyl group; Y represents a group

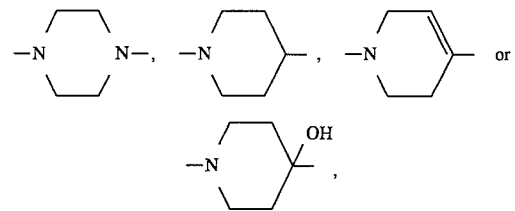

and Q represents —O— or a single bond, Z represents a C1 to C3 alkylene group or a group

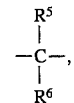

in which $R^5$ and $R^6$ each independently represents an alkyl group; $R^4$ represents a hydroxyl group, an alkoxy group or a group —NH(CH$_2$)$_m$COOH, in which m is a number of 1 to 3.

Another object of the present invention is to provide a therapeutic agent for hyperlipemia which comprises the above-described arylamide derivative (1) or a physiologically acceptable salt thereof as an active component of the agent.

A further object of the present invention is to provide a use of the above-described arylamide derivative (1) or a physiologically acceptable salt thereof as an active component in pharmaceuticals.

A still further object of the present invention is to provide a method for treating hyperlipemia which comprises administering the above-described arylamide derivative (1) or a physiologically acceptable salt thereof as an active component to a subject in need thereof.

DETAILED DESCRIPTION OF THE INVENTION AND PREFERRED EMBODIMENTS

In formula (1), the alkyl group is preferably linear or branched, and has 1 to 6 carbon atoms (hereinafter may be referred to as C1 to C6, and similar simplification will be employed throughout the specification). Specific examples of the alkyl group include a methyl group, an ethyl group, a n-propyl group, an i-propyl group, a n-butyl group, an i-butyl group, a t-butyl group, a n-pentyl group, an i-pentyl group, a n-hexyl group and the like. Examples of the halogen atom include a fluorine atom, a chlorine atom, a bromine atom and an iodine atom. The alkyl group substituted by a halogen atom is preferably a C1 to C6 linear or branched alkyl group substituted by 1 to 3 halogen atoms, and specific examples thereof include a trifluoromethyl group, a 1,1,1-trifluoroethyl group and the like. The carboxyalkyloxy group preferably has 2 to 7 carbon atoms in total, and specific examples thereof include carboxymethyloxy group, carboxyethyloxy group, carboxypropyloxy group and the like. The alkoxy group is preferably a C1 to C6 linear or branched group and specific examples thereof include a methoxy group, an ethoxy group, a n-propyloxy group, an i-propyloxy group, a n-butyloxy group, an i-butyloxy group, a t-butyloxy group, a n-pentyloxy group, an i-pentyloxy group, a n-hexyloxy group and the like. The alkenyl group preferably has 2 to 6 carbon atoms, and specific examples of the alkenyl group include a vinyl group, a propenyl group, an allyl group, a butenyl group, a pentenyl group and the like. The acylamino group is preferably an alkanoylamino group having 2 to 6 carbon atoms, and specific examples thereof include a formyl amino group, an acetamino group, a propionylamino group, a butyrylamino group and the like. Examples of C1 to C3 alkylene group include a methylene group, an ethylene group and a propylene group.

Furthermore, in formula (1), preferable examples of Ar include a group

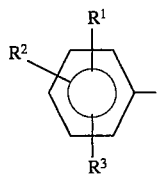

or a pyridinyl group, more preferably a group

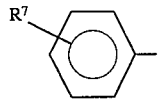

in which $R^7$ represents a hydrogen atom, a halogen atom or an alkyl group, and most preferably a phenyl group substituted by a halogen atom. Examples of Y which are particularly preferred include a group

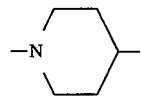

and

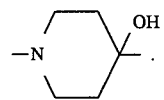

Examples of Q which are particularly preferred include —O—. Preferable examples of Z include a group

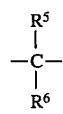

and in particular

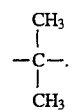

Preferable examples of $R^4$ include a hydroxyl group and an alkoxy group, and in particular a hydroxyl group.

No particular limitation is imposed on the salts of the arylamide derivative (1) as long as they are physiologically acceptable, and examples of the salts include alkali metal salts, inorganic acid salts, organic acid salts and the like. Specific examples of the alkali metal salts include lithium salts, sodium salts, potassium salts, magnesium salts and the like. Specific examples of inorganic acid salts include hydrochlorides, sulfates, nitrates, hydrobromates, phosphates and the like. Specific examples of the organic acid salts include acetates, oxalates, citrates, malates, fumarates, maleates, succinates, lactates, tartarates, methanesulfonates, benzenesulfonates, p-toluenesulfonates and the like.

Specific examples of the compounds of formula (1) according to the present invention include the following:
2-(1-benzoylpiperidin-4-yl)α,α-dimethylphenoxyacetic acid,
4-(1-benzoylpiperidin-4-yl)α,α-dimethylphenoxyacetic acid,
Isopropyl 3-(1-benzoylpiperidin-4-yl)α,α-dimethylphenoxyacetate,
2-{1-(4-methylbenzoyl)piperidin-4-yl}α,α-dimethylphenoxyacetic acid,
4-{1-(4-methylbenzoyl)piperidin-4-yl}α,α-dimethylphenoxyacetic acid,
Isopropyl 3-{1-(4-methylbenzoyl)piperidin-4-yl}α,α-dimethylphenoxyacetate,
2-{1-(4-methoxybenzoyl)piperidin-4-yl}α,α-dimethylphenoxyacetic acid,
3-{1-(4-methoxybenzoyl)piperidin-4-yl}α,α-dimethylphenoxyacetic acid,
4-{1-(4-methoxybenzoyl)piperidin-4-yl}α,α-dimethylphenoxyacetic acid,
Isopropyl 3-{1-(4-methoxybenzoyl)piperidin-4-yl}α,α-dimethylphenoxyacetate,
2-{1-(4-fluorobenzoyl)piperidin-4-yl}α,α-dimethylphenoxyacetic acid,
3-{1-(4-fluorobenzoyl)piperidin-4-yl}α,α-dimethylphenoxyacetic acid,
4-{1-(4-fluorobenzoyl)piperidin-4-yl}α,α-dimethylphenoxyacetic acid,
Isopropyl 3-{1-(4-fluorobenzoyl)piperidin-4-yl}α,α-dimethylphenoxyacetate,
2-{1-(4-chlorobenzoyl)piperidin-4-yl}α,α-dimethylphenoxyacetic acid,
3-{1-(4-chlorobenzoyl)piperidin-4-yl}α,α-dimethylphenoxyacetic acid,
4-{1-(4-chlorobenzoyl)piperidin-4-yl}α,α-dimethylphenoxyacetic acid,
Isopropyl 3-{1-(4-chlorobenzoyl)piperidin-4-yl}α,α-dimethylphenoxyacetate,
2-{1-(4-bromobenzoyl)piperidin-4-yl}α,α-dimethylphenoxyacetic acid,
4-{1-(4-bromobenzoyl)piperidin-4-yl}α,α-dimethylphenoxyacetic acid,
Isopropyl 3-{1-(4-bromobenzoyl)piperidin-4-yl}α,α-dimethylphenoxyacetate,
2-{1-(4-iodobenzoyl)piperidin-4-yl}α,α-dimethylphenoxyacetic acid,
3-{1-(4-iodobenzoyl)piperidin-4-yl}α,α-dimethylphenoxyacetic acid, 4-{1-(4-iodobenzoyl)piperidin-4-yl}α,α-dimethylphenoxyacetic acid,
Isopropyl 3-{1-(4-iodobenzoyl)piperidin-4-yl}α,α-dimethylphenoxyacetate,
2-{1-(4-trifluoromethylbenzoyl)piperidin-4-yl}α,α-dimethylphenoxyacetic acid,
3-{1-(4-trifluoromethylbenzoyl)piperidin-4-yl}α,α-dimethylphenoxyacetic acid,
4-{1-(4-trifluoromethylbenzoyl)piperidin-4-yl}α,α-dimethylphenoxyacetic acid,
Isopropyl 3-{1-(4-trifluoromethylbenzoyl)piperidin-4-yl}α, α-dimethylphenoxyacetate,
2-{1-(4-hydroxy-3,5-diiodobenzoyl)piperidin-4-yl}α,α-dimethylphenoxyacetic acid,
3-{1-(4-hydroxy-3,5-diiodobenzoyl)piperidin-4-yl}α,α-dimethylphenoxyacetic acid,
4-{1-(4-hydroxy-3,5-diiodobenzoyl)piperidin-4-yl}α,α-dimethylphenoxyacetic acid,
Isopropyl 3-{1-(4-hydroxy-3,5-diiodobenzoyl)piperidin-4-yl}α,α-dimethylphenoxyacetate,
2-{1-(3,5-di-t-butyl-4-hydroxybenzoyl)piperidin-4-yl}α,α-dimethylphenoxyacetic acid,
3-{1-(3,5-di-t-butyl-4-hydroxybenzoyl)piperidin-4-yl}α,α-dimethylphenoxyacetic acid,
4-{1-(3,5-di-t-butyl-4-hydroxybenzoyl)piperidin-4-yl}α,α-dimethylphenoxyacetic acid,
Isopropyl 3-{1-(3,5-di-t-butyl-4-hydroxybenzoyl)piperidin-4 -yl}α,α-dimethylphenoxyacetate,
2-(1-nicotinoylpiperidin-4-yl)α,α-dimethylphenoxyacetic acid,
3-(1-nicotinoylpiperidin-4-yl)α,α-dimethylphenoxyacetic acid,
4-(1-nicotinoylpiperidin-4-yl)α,α-dimethylphenoxyacetic acid,
Isopropyl 3-(1-nicotinoylpiperidin-4-yl)α,α-dimethylphenoxyacetate,
2-(1-isonicotinoylpiperidin-4-yl)α,α-dimethylphenoxyacetic acid,
3-(1-isonicotinoylpiperidin-4-yl)α,α-dimethylphenoxyacetic acid,
4-(1-isonicotinoylpiperidin-4-yl)α,α-dimethylphenoxyacetic acid,
Isopropyl 3-(1-isonicotinoylpiperidin-4-yl)α,α-dimethylphenoxyacetate,
2-{1-(2-furancarbonyl)piperidin-4-yl}α,α-dimethylphenoxyacetic acid,
3-{1-(2-furancarbonyl)piperidin-4-yl}α,α-dimethylphenoxyacetic acid,
4-{1-(2-furancarbonyl)piperidin-4-yl}α,α-dimethylphenoxyacetic acid,
Isopropyl 3-{1-(2-furancarbonyl)piperidin-4-yl}α,α-dimethylphenoxyacetate,
2-{1-(2-thenoyl)piperidin-4-yl}α,α-dimethylphenoxyacetic acid,
3-{1-(2-thenoyl)piperidin-4-yl}α,α-dimethylphenoxyacetic acid,
4-{1-(2-thenoyl)piperidin-4-yl}α,α-dimethylphenoxyacetic acid,
Isopropyl 3-{1-(2-thenoyl)piperidin-4-yl}α,α-dimethylphenoxyacetate,
{2-(4-benzoylpiperazinyl)phenoxy}α,α-dimethylacetic acid,
{4-(4-benzoylpiperazinyl)phenoxy}α,α-dimethylacetic acid,
Isopropyl {3-(4-benzoylpiperazinyl)phenoxy}α,α-dimethylacetate,
[2-{4-(4-methylbenzoyl)piperazinyl}phenoxy]α,α-dimethylacetic acid,
[4-{4-(4-methylbenzoyl)piperazinyl}phenoxy]α,α-dimethylacetic acid,
Isopropyl [3-{4-(4-methylbenzoyl)piperazinyl}phenoxy]α, α-dimethylacetate,
[2-{4-(4-methoxybenzoyl)piperazinyl}phenoxy]α,α-dimethylacetic acid,
[3-{4-(4-methoxybenzoyl)piperazinyl}phenoxy]α,α-dimethylacetic acid,
[4-{4-(4-methoxybenzoyl)piperazinyl}phenoxy]α,α-dimethylacetic acid,
Isopropyl [3-{4-(4-methoxybenzoyl)piperazinyl}phenoxy] α,α-dimethylacetate,
[2-{4-(4-fluorobenzoyl)piperazinyl}phenoxy]α,α-dimethylacetic acid,
[3-{4-(4-fluorobenzoyl)piperazinyl}phenoxy]α,α-dimethylacetic acid,
[4-{4-(4-fluorobenzoyl)piperazinyl}phenoxy]α,α-dimethylacetic acid,
Isopropyl [3-{4-(4-fluorobenzoyl)piperazinyl}phenoxy]α, α-dimethylacetate,
[2-{4-(4-chlorobenzoyl)piperazinyl}phenoxy]α,α-dimethylacetic acid,
[3-{4-(4-chlorobenzoyl)piperazinyl}phenoxy]α,α-dimethylacetic acid,
[4-{4-(4-chlorobenzoyl)piperazinyl}phenoxy]α,α-dimethylacetic acid,
Isopropyl [3-{4-(4-chlorobenzoyl)piperazinyl}phenoxy]α, α-dimethylacetate,
[2-{4-(4-bromobenzoyl)piperazinyl}phenoxy]α,α-dimethylacetic acid,
[4-{4-(4-bromobenzoyl)piperazinyl}phenoxy]α,α-dimethylacetic acid,
Isopropyl [3-{4-(4-bromobenzoyl)piperazinyl}phenoxy]α, α-dimethylacetate,
[2-{4-(4-iodobenzoyl)piperazinyl}phenoxy]α,α-dimethylacetic acid,
[3-{4-(4-iodobenzoyl)piperazinyl}phenoxy]α,α-dimethylacetic acid,
[4-{4-(4-iodobenzoyl)piperazinyl}phenoxy]α,α-dimethylacetic acid,
Isopropyl [3-{4-(4-iodobenzoyl)piperazinyl}phenoxy]α,α-dimethylacetate,
[2-{4-(4-trifluoromethylbenzoyl)piperazinyl}phenoxy]α,α-dimethylacetic acid,
[3-{4-(4-trifluoromethylbenzoyl)piperazinyl}phenoxy]α,α-dimethylacetic acid, [4-{4-(4-trifluoromethylbenzoyl)piperazinyl}phenoxy]α,α- dimethylacetic acid,
Isopropyl [3-{4-(4-trifluoromethylbenzoyl)piperazinyl}phenoxy]α,α-dimethylacetate,
[2-{4-(4-hydroxy-3,5-diiodobenzoyl)piperazinyl}phenoxy] α,α-dimethylacetic acid,
[3-{4-(4-hydroxy-3,5-diiodobenzoyl)piperazinyl}phenoxy] α,α-dimethylacetic acid,
[4-{4-(4-hydroxy-3,5-diiodobenzoyl)piperazinyl}phenoxy] α,α-dimethylacetic acid, Isopropyl [3-{4-(4-hydroxy-3,5 -diiodobenzoyl)piperazinyl}phenoxy]α,α- dimethylacetate,
[2-{4-(3,5-di-t-butyl-4-hydroxybenzoyl)piperazinyl}phenoxy]α,α-dimethylacetic acid, [3-{4-(3,5-di-t-butyl-4 -hydroxybenzoyl)piperazinyl}phenoxy]α,α- dimethylacetic acid,
[4-{4-(3,5-di-t-butyl-4-hydroxybenzoyl)piperazinyl}phenoxy]α,α-dimethylacetic acid, Isopropyl [3-{4-(3,5-di-t-butyl-4-hydroxybenzoyl)piperazinyl}phenoxy]α,α-dimethylacetate,
{2-(4-nicotinoylpiperazinyl)phenoxy}α,α-dimethylacetic acid,
{3-(4-nicotinoylpiperazinyl)phenoxy}α,α-dimethylacetic acid,
{4-(4-nicotinoylpiperazinyl)phenoxy}α,α-dimethylacetic acid,
Isopropyl {3-(4-nicotinoylpiperazinyl)phenoxy}α,α-dimethylacetate,
{2-(4-isonicotinoylpiperazinyl)phenoxy}α,α-dimethylacetic acid,
{3-(4-isonicotinoylpiperazinyl)phenoxy}α,α-dimethylacetic acid,
{4-(4-isonicotinoylpiperazinyl)phenoxy}α,α-dimethylacetic acid,
Isopropyl {3-(4-isonicotinoylpiperazinyl)phenoxy}α,α-dimethylacetate,
[2-{4-(2-furancarbonyl)piperazinyl}phenoxy]α,α-dimethylacetic acid,
[3-{4-(2-furancarbonyl)piperazinyl}phenoxy]α,α-dimethylacetic acid,
[4-{4-(2-furancarbonyl)piperazinyl}phenoxy]α,α-dimethylacetic acid,
Isopropyl [3-{4-(2-furancarbonyl)piperazinyl}phenoxy]α,α-dimethylacetate,
[2-{4-(2-thenoyl)piperazinyl}phenoxy]α,α-dimethylacetic acid,
[3-{4-(2-thenoyl)piperazinyl}phenoxy]α,α-dimethylacetic acid,
[4-{4-(2-thenoyl)piperazinyl}phenoxy]α,α-dimethylacetic acid,
Isopropyl [3-{4-(2-thenoyl)piperazinyl}phenoxy]α,α-dimethylacetate,
2-(1-benzoylpiperidin-3-en-4-yl)α,α-dimethylphenoxyacetic acid,
3-(1-benzoylpiperidin-3-en-4-yl)α,α-dimethylphenoxyacetic acid,
4-(1-benzoylpiperidin-3-en-4-yl)α,α-dimethylphenoxyacetic acid,
Isopropyl 3-(1-benzoylpiperidin-3-en-4-yl)α,α-dimethylphenoxyacetate,
2-{1-(4-methylbenzoyl)piperidin-3-en-4-yl}α,α-dimethylphenoxyacetic acid,
3-{1-(4-methylbenzoyl)piperidin-3-en-4-yl}α,α-dimethylphenoxyacetic acid,
4-{1-(4-methylbenzoyl)piperidin-3-en-4-yl}α,α-dimethylphenoxyacetic acid,
Isopropyl 3-{1-(4-methylbenzoyl)piperidin-3-en-4-yl}α,α-dimethylphenoxyacetate,
2-{1-(4-methoxybenzoyl)piperidin-3-en-4-yl}α,α-dimethylphenoxyacetic acid,
3-{1-(4-methoxybenzoyl)piperidin-3-en-4-yl}α,α-dimethylphenoxyacetic acid,
4-{1-(4-methoxybenzoyl)piperidin-3-en-4-yl}α,α-dimethylphenoxyacetic acid,
Isopropyl 3-{1-(4-methoxybenzoyl)piperidin-3-en-4-yl}α,α-dimethylphenoxyacetate,
2-{1-(4-fluorobenzoyl)piperidin-3-en-4-yl}α,α-dimethylphenoxyacetic acid,
3-{1-(4-fluorobenzoyl)piperidin-3-en-4-yl}α,α-dimethylphenoxyacetic acid,
4-{1-(4-fluorobenzoyl)piperidin-3-en-4-yl}α,α-dimethylphenoxyacetic acid,
Isopropyl 3-{1-(4-fluorobenzoyl)piperidin-3-en-4-yl}α,α-dimethylphenoxyacetate,
2-{1-(4-chlorobenzoyl)piperidin-3-en-4-yl}α,α-dimethylphenoxyacetic acid,
3-{1-(4-chlorobenzoyl)piperidin-3-en-4-yl}α,α-dimethylphenoxyacetic acid,
4-{1-(4-chlorobenzoyl)piperidin-3-en-4-yl}α,α-dimethylphenoxyacetic acid,
Isopropyl 3-{1-(4-chlorobenzoyl)piperidin-3-en-4-yl}α,α-dimethylphenoxyacetate,
4-{1-(4-bromobenzoyl)piperidin-3-en-4-yl}α,α-dimethylphenoxyacetic acid,
2-{1-(4-iodobenzoyl)piperidin-3-en-4-yl}α,α-dimethylphenoxyacetic acid,
3-{1-(4-iodobenzoyl)piperidin-3-en-4-yl}α,α-dimethylphenoxyacetic acid,
4-{1-(4-iodobenzoyl)piperidin-3-en-4-yl}α,α-dimethylphenoxyacetic acid,
Isopropyl 3-{1-(4-iodobenzoyl)piperidin-3-en-4-yl}α,α-dimethylphenoxyacetate,
2-{1-(4-trifluoromethylbenzoyl)piperidin-3-en-4-yl}α,α-dimethylphenoxyacetic acid,
3-{1-(4-trifluoromethylbenzoyl)piperidin-3-en-4-yl}α,α-dimethylphenoxyacetic acid,
4-{1-(4-trifluoromethylbenzoyl)piperidin-3-en-4-yl}α,α-dimethylphenoxyacetic acid,
Isopropyl 3-{1-(4-trifluoromethylbenzoyl)piperidin-3-en-4-yl}α,α-dimethylphenoxyacetate,
2-{1-(4-hydroxy-3,5-diiodobenzoyl)piperidin-3-en-4-yl}α,α-dimethylphenoxyacetic acid,
3-{1-(4-hydroxy-3,5-diiodobenzoyl)piperidin-3-en-4-yl}α,α-diemthylphenoxyaxetic acid,
4-{1-(4-hydroxy-3,5-diiodobenzoyl)piperidin-3-en-4-yl}α,α-dimethylphenoxyacetic acid,
Isopropyl 3-{1-(4-hydroxy-3,5-diiodobenzoyl)piperidin-3-en-4-yl}α,α-dimethylphenoxyacetate,
2-{1-(3,5-di-t-butyl-4-hydroxybenzoyl)piperidin-3-en-4-yl}α,α-dimethylphenoxyacetic acid,
3-{1-(3,5-di-t-butyl-4-hydroxybenzoyl)piperidin-3-en-4-yl}α,α-dimethylphenoxyacetic acid,
4-{1-(3,5-di-t-butyl-4-hydroxybenzoyl)piperidin-3-en-4-yl}α,α-dimethylphenoxyacetic acid,
Isopropyl 3-{1-(3,5-di-t-butyl-4-hydroxybenzoyl)piperidin-3-en-4-yl}α,α-dimethylphenoxyacetate,
2-(1-nicotinoylpiperidin-3-en-4-yl)α,α-dimethylphenoxyacetic acid,
3-(1-nicotinoylpiperidin-3-en-4-yl)α,α-dimethylphenoxyacetic acid,
4-(1-nicotinoylpiperidin-3-en-4-yl)α,α-dimethylphenoxyacetic acid,
Isopropyl 3-(1-nicotinoylpiperidin-3-en-4-yl)α,α-dimethylphenoxyacetate,
2-(1-isonicotinoylpiperidin-3-en-4-yl)α,α-dimethylphenoxyacetic acid,
3-(1-isonicotinoylpiperidin-3-en-4-yl)α,α-dimethylphenoxyacetic acid,
4-(1-isonicotinoylpiperidin-3-en-4-yl)α,α-dimethylphenoxyacetic acid,
Isopropyl 3-(1-isonicotinoylpiperidin-3-en-4-yl)α,α-dimethylphenoxyacetate,
2-{1-(2-furancarbonyl)piperidin-3-en-4-yl}α,α-dimethylphenoxyacetic acid,
3-{1-(2-furancarbonyl)piperidin-3-en-4-yl}α,α-dimethylphenoxyacetic acid,
4-{1-(2-furancarbonyl)piperidin-3-en-4-yl}α,α-dimethylphenoxyacetic acid,
Isopropyl 3-{1-(2-furancarbonyl)piperidin-3-en-4-yl}α,α-dimethylphenoxyacetate,
2-{1-(2-thenoyl)piperidin-3-en-4-yl}α,α-dimethylphenoxyacetic acid, 3-{1-(2-thenoyl)piperidin-3-en-4-yl}α,α-dimethylphenoxyacetic acid,
4-{1-(2-thenoyl)piperidin-3-en-4-yl}α,α-dimethylphenoxyacetic acid,
Isopropyl 3-{1-(2-thenoyl)piperidin-3-en-4-yl}α,α-dimethylphenoxyacetate,
2-{1-(4-methylbenzoyl)-4-hydroxypiperidin-4-yl}α,α-dimethylphenoxyacetic acid,
3-{1-(4-methylbenzoyl)-4-hydroxypiperidin-4-yl}α,α-dimethylphenoxyacetic acid,
4-{1-(4-methylbenzoyl)-4-hydroxypiperidin-4-yl}α,α-dimethylphenoxyacetic acid,
Isopropyl 3-{1-(4-methylbenzoyl)-4-hydroxypiperidin-4-yl}α,α-dimethylphenoxyacetate,
2-{1-(4-methoxybenzoyl)-4-hydroxypiperidin-4-yl}α,α-dimethylphenoxyacetic acid,
3-{1-(4-methoxybenzoyl)-4-hydroxypiperidin-4-yl}α,α-dimethylphenoxyacetic acid,
4-{1-(4-methoxybenzoyl)-4-hydroxypiperidin-4-yl}α,α-dimethylphenoxyacetic acid,
Isopropyl 3-{1-(4-methoxybenzoyl)-4-hydroxypiperidin-4-yl}α,α-dimethylphenoxyacetate,
2-{1-(4-trifluoromethylbenzoyl)-4-hydroxypiperidin-4-yl}α,α-dimethylphenoxyacetic acid,
3-{1-(4-trifluoromethylbenzoyl)-4-hydroxypiperidin-4-yl}α,α-dimethylphenoxyacetic acid,
4-{1-(4-trifluoromethylbenzoyl)-4-hydroxypiperidin-4-yl}α,α-dimethylphenoxyacetic acid,
Isopropyl 3-{1-(4-trifluoromethylbenzoyl)-4-hydroxypiperidin- 4-yl}α,α-dimethylphenoxyacetate,
2-{1-(4-hydroxy-3,5-diiodobenzoyl)-4-hydroxypiperidin-4-yl}α,α-dimethylphenoxyacetic acid,
3-{1-(4-hydroxy-3,5-diiodobenzoyl)-4-hydroxypiperidin-4-yl}α,α-dimethylphenoxyacetic acid,
4-{1-(4-hydroxy-3,5-diiodobenzoyl)-4-hydroxypiperidin-4-yl}α,α-dimethylphenoxyacetic acid,
Isopropyl 3-{1-(4-hydroxy-3,5-diiodobenzoyl)-4-hydroxypiperidin-4- yl}α,α-dimethylphenoxyacetate, 2-{1-(3,5-di-t-butyl- 4-hydroxybenzoyl)-4-hydroxypiperidin-4-yl}α,α-dimethylphenoxyacetic acid,
3-{1-(3,5-di-t-butyl-4-hydroxybenzoyl)-4-hydroxypiperidin-4 -yl}α,α-dimethylphenoxyacetic acid,
4-{1-(3,5-di-t-butyl-4-hydroxybenzoyl)-4-hydroxypiperidin-4 -yl}α,α-dimethylphenoxyacetic acid,
Isopropyl 3-{1-(3,5-di-t-butyl-4-hydroxybenzoyl)-4 -hydroxypiperidin-4-yl}α,α-dimethylphenoxyacetate,
2-(1-isonicotinoyl-4-hydroxypiperidin-4-yl)α,α-dimethylphenoxyacetic acid,
3-(1-isonicotinoyl-4-hydroxypiperidin-4-yl)α,α-dimethylphenoxyacetic acid,
4-(1-isonicotinoyl-4-hydroxypiperidin-4-yl)α,α-dimethylphenoxyacetic acid,
Isopropyl 3-(1-isonicotinoyl-4-hydroxypiperidin-4-yl)α,α-dimethylphenoxyacetate,
2-{1-(2-furancarbonyl)-4-hydroxypiperidin-4-yl}α,α-dimethylphenoxyacetic acid,
3-{1-(2-furancarbonyl)-4-hydroxypiperidin-4-yl}α,α-dimethylphenoxyacetic acid,
4-{1-(2-furancarbonyl)-4-hydroxypiperidin-4-yl}α,α-dimethylphenoxyacetic acid,
Isopropyl 3-{1-(2-furancarbonyl)-4-hydroxypiperidin-4-yl}α,α-dimethylphenoxyacetate,
2-{1-(2-thenoyl)piperidin-4-hydroxypiperidin-4-yl}α,α-dimethylphenoxyacetic acid,
3-{1-(2-thenoyl)piperidin-4-hydroxypiperidin-4-yl}α,α-dimethylphenoxyacetic acid,
4-{1-(2-thenoyl)piperidin-4-hydroxypiperidin-4-yl}α,α-dimethylphenoxyacetic acid,
Isopropyl 3-{1-(2-thenoyl)piperidin-4-hydroxypiperidin-4-yl}α,α-dimethylphenoxyacetate,
2-(4-benzoylpiperazinyl)β-phenoxypropionic acid,
3-(4-benzoylpiperazinyl)β-phenoxypropionic acid,
4-(4-benzoylpiperazinyl)β-phenoxypropionic acid,
2-{4-(4-bromobenzoyl)piperazinyl}β-phenoxypropionic acid,
3-{4-(4-bromobenzoyl)piperazinyl}β-phenoxypropionic acid,
4-{4-(4-bromobenzoyl)piperazinyl}β-phenoxypropionic acid,
2-(1-benzoylpiperidin-4-yl)β-phenoxypropionic acid,
3-(1-benzoylpiperidin-4-yl)β-phenoxypropionic acid,
4-(1-benzoylpiperidin-4-yl)β-phenoxypropionic acid,
2-{1-(4-bromobenzoyl)piperidin-4-yl}β-phenoxypropionic acid,
3-{1-(4-bromobenzoyl)piperidin-4-yl}β-phenoxypropionic acid,
4-{1-(4-bromobenzoyl)piperidin-4-yl}β-phenoxypropionic acid,
2-(1-benzoylpiperidin-3-en-4-yl)β-phenoxypropionic acid,
3-(1-benzoylpiperidin-3-en-4-yl)β-phenoxypropionic acid,
4-(1-benzoylpiperidin-3-en-4-yl)β-phenoxypropionic acid,
2-{1-(4-bromobenzoyl)piperidin-3-en-4-yl}β-phenoxypropionic acid,
3-{1-(4-bromobenzoyl)piperidin-3-en-4-yl}β-phenoxypropionic acid,
4-{1-(4-bromobenzoyl)piperidin-3-en-4-yl}β-phenoxypropionic acid,
2-(1-benzoyl-4-hydroxypiperidin-4-yl)β-phenoxypropionic acid,
3-(1-benzoyl-4-hydroxypiperidin-4-yl)β-phenoxypropionic acid,
4-(1-benzoyl-4-hydroxypiperidin-4-yl)β-phenoxypropionic acid,
2-{1-(4-bromobenzoyl)-4-hydroxypiperidin-4-yl}β-phenoxypropionic acid,
3-{1-(4-bromobenzoyl)-4-hydroxypiperidin-4-yl}β-phenoxypropionic acid,
4-{1-(4-bromobenzoyl)-4-hydroxypiperidin-4-yl}β-phenoxypropionic acid,
2-{4-(1-naphthalenecarbonyl)piperazinyl}phenoxyacetic acid,
2-{4-(1-naphthalenecarbonyl)piperazinyl}β-phenoxypropionic acid,
2-{4-(1-naphthalenecarbonyl)piperazinyl}γ-phenoxybutyric acid,
3-{4-(1-naphthalenecarbonyl)piperazinyl}phenoxyacetic acid,
3-{4-(1-naphthalenecarbonyl)piperazinyl}β-phenoxypropionic acid,
3-{4-(1-naphthalenecarbonyl)piperazinyl}γ-phenoxybutyric acid,
4-{4-(1-naphthalenecarbonyl)piperazinyl}phenoxyacetic acid,
4-{4-(1-naphthalenecarbonyl)piperazinyl}β-phenoxypropionic acid,
4-{4-(1-naphthalenecarbonyl)piperazinyl}γ-phenoxybutyric acid,
2-{4-(2-naphthalenecarbonyl)piperazinyl}phenoxyacetic acid,
2-{4-(2-naphthalenecarbonyl)piperazinyl}β-phenoxypropionic acid,
2-{4-(2-naphthalenecarbonyl)piperazinyl}γ-phenoxybutyric acid,
3-{4-(2-naphthalenecarbonyl)piperazinyl}phenoxyacetic acid, 3-{4-(2-naphthalenecarbonyl)piperazinyl}β-phenoxypropionic acid,
3-{4-(2-naphthalenecarbonyl)piperazinyl}γ-phenoxybutyric acid,
4-{4-(2-naphthalenecarbonyl)piperazinyl}phenoxyacetic acid,
4-{4-(2-naphthalenecarbonyl)piperazinyl}β-phenoxypropionic acid,
4-{4-(2-naphthalenecarbonyl)piperazinyl}γ-phenoxybutyric acid,
2-{1-(1-naphthalenecarbonyl)piperidin-4-yl}phenoxyacetic acid,
2-{1-(1-naphthalenecarbonyl)piperidin-4-yl}β-phenoxypropionic acid,
2-{1-(1-naphthalenecarbonyl)piperidin-4-yl}γ-phenoxybutyric acid,
3-{1-(1-naphthalenecarbonyl)piperidin-4-yl}phenoxyacetic acid,
3-{1-(1-naphthalenecarbonyl)piperidin-4-yl}β-phenoxypropionic acid,
3-{1-(1-naphthalenecarbonyl)piperidin-4-yl}γ-phenoxybutyric acid,
4-{1-(1-naphthalenecarbonyl)piperidin-4-yl}phenoxyacetic acid,
4-{1-(1-naphthalenecarbonyl)piperidin-4-yl}β-phenoxypropionic acid,
4-{1-(1-naphthalenecarbonyl)piperidin-4-yl}γ-phenoxybutyric acid,
2-{1-(2-naphthalenecarbonyl)piperidin-4-yl}phenoxyacetic acid,
2-{1-(2-naphthalenecarbonyl)piperidin-4-yl}β-phenoxypropionic acid,
2-{1-(2-naphthalenecarbonyl)piperidin-4-yl}γ-phenoxybutyric acid,
3-{1-(2-naphthalenecarbonyl)piperidin-4-yl}phenoxyacetic acid,
3-{1-(2-naphthalenecarbonyl)piperidin-4-yl}β-phenoxypropionic acid,
3-{1-(2-naphthalenecarbonyl)piperidin-4-yl}γ-phenoxybutyric acid,
4-{1-(2-naphthalenecarbonyl)piperidin-4-yl}phenoxyacetic acid,
4-{1-(2-naphthalenecarbonyl)piperidin-4-yl}β-phenoxypropionic acid,
4-{1-(2-naphthalenecarbonyl)piperidin-4-yl}γ-phenoxybutyric acid,
2-{1-(1-naphthalenecarbonyl)piperidin-3-en-4-yl}phenoxyacetic acid,
2-{1-(1-naphthalenecarbonyl)piperidin-3-en-4-yl}β-phenoxypropionic acid,
2-{1-(1-naphthalenecarbonyl)piperidin-3-en-4-yl}γ-phenoxybutyric acid,
3-{1-(1-naphthalenecarbonyl)piperidin-3-en-4-yl}phenoxyacetic acid,
3-{1-(1-naphthalenecarbonyl)piperidin-3-en-4-yl}β-phenoxypropionic acid,
3-{1-(1-naphthalenecarbonyl)piperidin-3-en-4-yl}γ-phenoxybutyric acid,
4-{1-(1-naphthalenecarbonyl)piperidin-3-en-4-yl}phenoxyacetic acid,
4-{1-(1-naphthalenecarbonyl)piperidin-3-en-4-yl}β-phenoxypropionic acid,
4-{1-(1-naphthalenecarbonyl)piperidin-3-en-4-yl}γ-phenoxybutyric acid,
2-{1-(2-naphthalenecarbonyl)piperidin-3-en-4-yl}phenoxyacetic acid,
2-{1-(2-naphthalenecarbonyl)piperidin-3-en-4-yl}β-phenoxypropionic acid,
2-{1-(2-naphthalenecarbonyl)piperidin-3-en-4-yl}γ-phenoxybutyric acid,
3-{1-(2-naphthalenecarbonyl)piperidin-3-en-4-yl}phenoxyacetic acid,
3-{1-(2-naphthalenecarbonyl)piperidin-3-en-4-yl}β-phenoxypropionic acid,
3-{1-(2-naphthalenecarbonyl)piperidin-3-en-4-yl}γ-phenoxybutyric acid,
4-{1-(2-naphthalenecarbonyl)piperidin-3-en-4-yl}phenoxyacetic acid,
4-{1-(2-naphthalenecarbonyl)piperidin-3-en-4-yl}β-phenoxypropionic acid,
4-{1-(2-naphthalenecarbonyl)piperidin-3-en-4-yl}γ-phenoxybutyric acid,
2-{1-(2-naphthalenecarbonyl)-4-hydroxypiperidin-4-yl}phenoxyacetic acid,
2-{1-(2-naphthalenecarbonyl)-4-hydroxypiperidin-4-yl}β-phenoxypropionic acid,
2-{1-(2-naphthalenecarbonyl)-4-hydroxypiperidin-4-yl}γ-phenoxybutyric acid,
3-{1-(2-naphthalenecarbonyl)-4-hydroxypiperidin-4-yl}phenoxyacetic acid,
3-{1-(2-naphthalenecarbonyl)-4-hydroxypiperidin-4-yl}β-phenoxypropionic acid,
3-{1-(2-naphthalenecarbonyl)-4-hydroxypiperidin-4-yl}γ-phenoxybutyric acid,
4-{1-(2-naphthalenecarbonyl)-4-hydroxypiperidin-4-yl}phenoxyacetic acid,
4-{1-(2-naphthalenecarbonyl)-4-hydroxypiperidin-4-yl}β-phenoxypropionic acid,
4-{1-(2-naphthalenecarbonyl)-4-hydroxypiperidin-4-yl}γ-phenoxybutyric acid,
2-{1-(1-naphthalenecarbonyl)-4-hydroxypiperidin-4-yl}phenoxyacetic acid,
2-{1-(1-naphthalenecarbonyl)-4-hydroxypiperidin-4-yl}β-phenoxypropionic acid,
2-{1-(1-naphthalenecarbonyl)-4-hydroxypiperidin-4-yl}γ-phenoxybutyric acid,
3-{1-(1-naphthalenecarbonyl)-4-hydroxypiperidin-4-yl}phenoxyacetic acid,
3-{1-(1-naphthalenecarbonyl)-4-hydroxypiperidin-4-yl}β-phenoxypropionic acid,
3-{1-(1-naphthalenecarbonyl)-4-hydroxypiperidin-4-yl}γ-phenoxybutyric acid,
4-{1-(1-naphthalenecarbonyl)-4-hydroxypiperidin-4-yl}phenoxyacetic acid,
4-{1-(1-naphthalenecarbonyl)-4-hydroxypiperidin-4-yl}β-phenoxypropionic acid,
4-{1-(1-naphthalenecarbonyl)-4-hydroxypiperidin-4-yl}γ-phenoxybutyric acid,
2-{1-(1-naphthalenecarbonyl)-4-hydroxypiperidin-4-yl}α,α-dimethylphenoxyacetic acid,
3-{1-(1-naphthalenecarbonyl)-4-hydroxypiperidin-4-yl}α,α-dimethylphenoxyacetic acid,
4-{1-(1-naphthalenecarbonyl)-4-hydroxypiperidin-4-yl}α,α-dimethylphenoxyacetic acid,
2-{1-(2-naphthalenecarbonyl)-4-hydroxypiperidin-4-yl}α,α-dimethylphenoxyacetic acid,
3-{1-(2-naphthalenecarbonyl)-4-hydroxypiperidin-4-yl}α,α-dimethylphenoxyacetic acid,
4-{1-(2-naphthalenecarbonyl)-4-hydroxypiperidin-4-yl}α,α-dimethylphenoxyacetic acid,
2-{4-(1-naphthalenecarbonyl)piperazinyl}phenylacetic acid,
2-{4-(1-naphthalenecarbonyl)piperazinyl}β-phenylpropionic acid,
2-{4-(1-naphthalenecarbonyl)piperazinyl}γ-phenylbutyric acid, 3-{4-(1-naphthalenecarbonyl)piperazinyl}phenylacetic acid,
3-{4-(1-naphthalenecarbonyl)piperazinyl}β-phenylpropionic acid,
3-{4-(1-naphthalenecarbonyl)piperazinyl}γ-phenylbutyric acid,
4-{4-(1-naphthalenecarbonyl)piperazinyl}phenylacetic acid,
4-{4-(1-naphthalenecarbonyl)piperazinyl}β-phenylpropionic acid,
4-{4-(1-naphthalenecarbonyl)piperazinyl}γ-phenylbutyric acid,
2-{4-(2-naphthalenecarbonyl)piperazinyl}phenylacetic acid,
2-{4-(2-naphthalenecarbonyl)piperazinyl}β-phenylpropionic acid,
2-{4-(2-naphthalenecarbonyl)piperazinyl}γ-phenylbutyric acid,
3-{4-(2-naphthalenecarbonyl)piperazinyl}phenylacetic acid,
3-{4-(2-naphthalenecarbonyl)piperazinyl}β-phenylpropionic acid,
3-{4-(2-naphthalenecarbonyl)piperazinyl}γ-phenylbutyric acid,
4-{4-(2-naphthalenecarbonyl)piperazinyl}phenylacetic acid,
4-{4-(2-naphthalenecarbonyl)piperazinyl}β-phenylpropionic acid,
4-{4-(2-naphthalenecarbonyl)piperazinyl}γ-phenylbutyric acid,
2-{1-(1-naphthalenecarbonyl)piperidin-4-yl}phenylacetic acid,
2-{1-(1-naphthalenecarbonyl)piperidin-4-yl}β-phenylpropionic acid,
2-{1-(1-naphthalenecarbonyl)piperidin-4-yl}γ-phenylbutyric acid,
3-{1-(1-naphthalenecarbonyl)piperidin-4-yl}phenylacetic acid,
3-{1-(1-naphthalenecarbonyl)piperidin-4-yl}β-phenylpropionic acid,
3-{1-(1-naphthalenecarbonyl)piperidin-4-yl}γ-phenylbutyric acid,
4-{1-(1-naphthalenecarbonyl)piperidin-4-yl}phenylacetic acid,
4-{1-(1-naphthalenecarbonyl)piperidin-4-yl}β-phenylpropionic acid,
4-{1-(1-naphthalenecarbonyl)piperidin-4-yl}γ-phenylbutyric acid,
2-{1-(2-naphthalenecarbonyl)piperidin-4-yl}phenylacetic acid,
2-{1-(2-naphthalenecarbonyl)piperidin-4-yl}β-phenylpropionic acid,
2-{1-(2-naphthalenecarbonyl)piperidin-4-yl}γ-phenylbutyric acid,
3-{1-(2-naphthalenecarbonyl)piperidin-4-yl}phenylacetic acid,
3-{1-(2-naphthalenecarbonyl)piperidin-4-yl}β-phenylpropionic acid,
3-{1-(2-naphthalenecarbonyl)piperidin-4-yl}γ-phenylbutyric acid,
4-{1-(2-naphthalenecarbonyl)piperidin-4-yl}phenylacetic acid,
4-{1-(2-naphthalenecarbonyl)piperidin-4-yl}β-phenylpropionic acid,
4-{1-(2-naphthalenecarbonyl)piperidin-4-yl}γphenylbutyric acid,
2-{1-(1-naphthalenecarbonyl)piperidin-3-en-4-yl}phenylacetic acid,
2-{1-(1-naphthalenecarbonyl)piperidin-3-en-4-yl}β-phenylpropionic acid,
2-{1-(1-naphthalenecarbonyl)piperidin-3-en-4-yl}γ-phenylbutyric acid,
3-{1-(1-naphthalenecarbonyl)piperidin-3-en-4-yl}phenylacetic acid,
3-{1-(1-naphthalenecarbonyl)piperidin-3-en-4-yl}β-phenylpropionic acid,
3-{1-(1-naphthalenecarbonyl)piperidin-3-en-4-yl}γ-phenylbutyric acid,
4-{1-(1-naphthalenecarbonyl)piperidin-3-en-4-yl}phenylacetic acid,
4-{1-(1-naphthalenecarbonyl)piperidin-3-en-4-yl}β-phenylpropionic acid,
4-{1-(1-naphthalenecarbonyl)piperidin-3-en-4-yl}γ-phenylbutyric acid,
2-{1-(2-naphthalenecarbonyl)-4-hydroxypiperidin-4-yl}phenylacetic acid,
2-{1-(2-naphthalenecarbonyl)-4-hydroxypiperidin-4-yl}β-phenylpropionic acid,
2-{1-(2-naphthalenecarbonyl)-4-hydroxypiperidin-4-yl}γ-phenylbutyric acid,
3-{1-(2-naphthalenecarbonyl)-4-hydroxypiperidin-4-yl}phenylacetic acid,
3-{1-(2-naphthalenecarbonyl)-4-hydroxypiperidin-4-yl}β-phenylpropionic acid,
3-{1-(2-naphthalenecarbonyl)-4-hydroxypiperidin-4-yl}γ-phenylbutyric acid,
4-{1-(2-naphthalenecarbonyl)-4-hydroxypiperidin-4-yl}phenylacetic acid,
4-{1-(2-naphthalenecarbonyl)-4-hydroxypiperidin-4-yl}β-phenylpropionic acid,
4-{1-(2-naphthalenecarbonyl)-4-hydroxypiperidin-4-yl}γ-phenylbutyric acid,
3-(4-nicotinoylpiperazinyl)phenoxyacetic acid,
3-(4-nicotinoylpiperazinyl)phenylacetic acid,
3-(1-nicotinoylpiperidin-4-yl)phenoxyacetic acid,
3-(1-nicotinoylpiperidin-4-yl)phenylacetic acid,
3-(1-nicotinoylpiperidin-3-en-4-yl)phenylacetic acid,
3-(1-nicotinoyl-4-hydroxypiperidin-4-yl)phenoxyacetic acid,
3-(1-nicotinoyl-4-hydroxypiperidin-4-yl)phenylacetic acid,
3-{4-(2-furancarbonyl)piperazinyl}phenoxyacetic acid,
3-{4-(2-furancarbonyl)piperazinyl}phenylacetic acid,
3-{1-(2-furancarbonyl)piperidin-4-yl}phenoxyacetic acid,
3-{1-(2-furancarbonyl)piperidin-4-yl}phenylacetic acid,
3-{1-(2-furancarbonyl)piperidin-3-en-4-yl}phenoxyacetic acid,
3-{1-(2-furancarbonyl)-4-hydroxypiperidin-4-yl}phenoxyacetic acid,
3-{1-(2-furancarbonyl)-4-hydroxypiperidin-4-yl}phenylacetic acid,
3-{1-(2-furancarbonyl)-4-hydroxypiperidin-4-yl}α,α-dimethylphenoxyacetic acid
3-{1-(2-furancarbonyl)piperidin-3-en-4-yl}phenylacetic acid,
3-(1-isonicotinoyl-4-hydroxypiperidin-4-yl}α,α-dimethylphenoxyacetic acid,
3-(4-thenoylpiperazinyl)phenoxyacetic acid,
3-(4-thenoylpiperazinyl)phenylacetic acid,
3-(1-thenoylpiperidin-4-yl)phenoxyacetic acid,
3-(1-thenoylpiperidin-4-yl)phenylacetic acid,
3-(1-thenoylpiperidin-3-en-4-yl)phenoxyacetic acid,
3-(1-thenoylpiperidin-3-en-4-yl)phenylacetic acid,
3-(1-thenoyl-4-hydroxypiperidin-4-yl)phenoxyacetic acid,
3-(1-thenoyl-4-hydroxypiperidin-4-yl)α,α-dimethylphenoxyacetic acid, 3-(1-thenoyl-4-hydroxypiperidin-4-yl)phenylacetic acid,
3-{4-(4-quinolinecarbonyl)piperazinyl}phenoxyacetic acid,
3-{4-(4-quinolinecarbonyl)piperazinyl}phenylacetic acid,
3-{1-(4-quinolinecarbonyl)piperidin-4-yl}phenoxyacetic acid,
3-{1-(4-quinolinecarbonyl)piperidin-4-yl}phenylacetic acid,
3-{1-(4-quinolinecarbonyl)-4-hydroxypiperidin-4-yl}phenoxyacetic acid,
3-{1-(4-quinolinecarbonyl)-4-hydroxypiperidin-4-yl}α,α-dimethylphenoxyacetic acid,
3-{1-(4-quinolinecarbonyl)-4-hydroxypiperidin-4-yl}phenylacetic acid,
3-{4-(2-indolecarbonyl)piperazinyl}phenoxyacetic acid,
3-{1-(2-indolecarbonyl)piperidin-4-yl}phenoxyacetic acid,
3-{1-(2-indolecarbonyl)-4-hydroxypiperidin-4-yl}phenoxyacetic acid,
3-{1-(2-indolecarbonyl)piperidin-3-en-4-yl}phenoxyacetic acid,
3-{1-(2-indolecarbonyl)-4-hydroxypiperidin-4-yl}α,α-dimethylphenoxyacetic acid,
2-{1-(3-indolecarbonyl)piperidin-4-yl}α,α-dimethylphenoxyacetic acid,
3-{1-(3-indolecarbonyl)piperidin-4-yl}α,α-dimethylphenoxyacetic acid,
4-{1-(3-indolecarbonyl)piperidin-4-yl}α,α-dimethylphenoxyacetic acid,
Isopropyl 3-{1-(3-indolecarbonyl)piperidin-4-yl}α,α-dimethylphenoxyacetate,
2-{1-(2-quinolinecarbonyl)piperidin-4-yl}α,α-dimethylphenoxyacetic acid,
3-{1-(2-quinolinecarbonyl)piperidin-4-yl}α,α-dimethylphenoxyacetic acid,
4-{1-(2-quinolinecarbonyl)piperidin-4-yl}α,α-dimethylphenoxyacetic acid,
Isopropyl 3-{1-(2-quinolinecarbonyl)piperidin-4-yl}α,α-dimethylphenoxyacetate,
2-{1-(1-naphthalenecarbonyl)piperidin-4-yl}α,α-dimethylphenoxyacetic acid,
3-{1-(1-naphthalenecarbonyl)piperidin-4-yl}α,α-dimethylphenoxyacetic acid,
4-{1-(1-naphthalenecarbonyl)piperidin-4-yl}α,α-dimethylphenoxyacetic acid,
Isopropyl 3-{1-(1-naphthalenecarbonyl)piperidin-4-yl}α,α-dimethylphenoxyacetate,
[2-{4-(3-indolecarbonyl)piperazinyl}phenoxy]α,α-dimethylacetic acid,
[3-{4-(3-indolecarbonyl)piperazinyl}phenoxy]α,α-dimethylacetic acid,
[4-{4-(3-indolecarbonyl)piperazinyl}phenoxy]α,α-dimethylacetic acid,
Isopropyl [3-{4-(3-indolecarbonyl)piperazinyl}phenoxy]α,α-dimethylacetate,
[2-{4-(2-quinolinecarbonyl)piperazinyl}phenoxy]α,α-dimethylacetic acid,
[3-{4-(2-quinolinecarbonyl)piperazinyl}phenoxy]α,α-dimethylacetic acid,
[4-{4-(2-quinolinecarbonyl)piperazinyl}phenoxy]α,α-dimethylacetic acid,
Isopropyl [3-{4-(2-quinolinecarbonyl)piperazinyl}phenoxy]α,α-dimethylacetate,
[2-{4-(1-naphthalenecarbonyl)piperazinyl}phenoxy]α,α-dimethylacetic acid,
[3-{4-(1-naphthalenecarbonyl)piperazinyl}phenoxy]α,α-dimethylacetic acid,
[4-{4-(1-naphthalenecarbonyl)piperazinyl}phenoxy]α,α-dimethylacetic acid,
Isopropyl [3-{4-(1-naphthalenecarbonyl)piperazinyl}phenoxy]α,α-dimethylacetate,2-{1-(3-indolecarbonyl)piperidin-3-en-4-yl}α,α-dimethyl-phenoxyacetic acid,
3-{1-(3-indolecarbonyl)piperidin-3-en-4-yl}α,α-dimethylphenoxyacetic acid,
4-{1-(3-indolecarbonyl)piperidin-3-en-4-yl}α,α-dimethylphenoxyacetic acid,
Isopropyl 3-{1-(3-indolecarbonyl)piperidin-3-en-4-yl}α,α-dimethylphenoxyacetate,
2-{1-(2-quinolinecarbonyl)piperidin-3-en-4-yl}α,α-dimethylphenoxyacetic acid,
3-{1-(2-quinolinecarbonyl)piperidin-3-en-4-yl}α,α-dimethylphenoxyacetic acid,
4-{1-(2-quinolinecarbonyl)piperidin-3-en-4-yl}α,α-dimethylphenoxyacetic acid,
Isopropyl 3-{1-(2-quinolinecarbonyl)piperidin-3-en-4-yl}α,α-dimethylphenoxyacetate,
2-{1-(1-naphthalenecarbonyl)piperidin-3-en-4-yl}α,α-dimethylphenoxyacetic acid,
3-{1-(1-naphthalenecarbonyl)piperidin-3-en-4-yl}α,α-dimethylphenoxyacetic acid,
4-{1-(1-naphthalenecarbonyl)piperidin-3-en-4-yl}α,α-dimethylphenoxyacetic acid,
Isopropyl 3-{1-(1-naphthalenecarbonyl)piperidin-3-en-4-yl}α,α-dimethylphenoxyacetate,
2-{1-(2,4-difluorobenzoyl)piperidin-4-yl}α,α-dimethylphenoxyacetic acid,
3-{1-(2,4-difluorobenzoyl)piperidin-4-yl}α,α-dimethylphenoxyacetic acid,
4-{1-(2,4-difluorobenzoyl)piperidin-4-yl}α,α-dimethylphenoxyacetic acid,
Isopropyl 3-{1-(2,4-difluorobenzoyl)piperidin-4-yl}α,α-dimethylphenoxyacetate,
[2-{4-(2,4-difluorobenzoyl)piperazinyl}phenoxy]α,α-dimethylacetic acid,
[3-{4-(2,4-difluorobenzoyl)piperazinyl}phenoxy]α,α-dimethylacetic acid,
[4-{4-(2,4-difluorobenzoyl)piperazinyl}phenoxy]α,α-dimethylacetic acid,
Isopropyl 3-{4-(2,4-difluorobenzoyl)piperazinyl}phenoxy] α,α-dimethylacetate,
2-{1-(2,4-difluorobenzoyl)piperidin-3-en-4-yl}α,α-dimethylphenoxyacetic acid,
3-{1-(2,4-difluorobenzoyl)piperidin-3-en-4-yl}α,α-dimethylphenoxyacetic acid,
4-{1-(2,4-difluorobenzoyl)piperidin-3-en-4-yl}α,α-dimethylphenoxyacetic acid,
Isopropyl 3-{1-(2,4-difluorobenzoyl)piperidin-4-yl}α,α-dimethylphenoxyacetate,
2-{1-(2,4-difluorobenzoyl)-4-hydroxypiperidin-4-yl}α,α-dimethylphenoxyacetic acid,
3-{1-(2,4-difluorobenzoyl)-4-hydroxypiperidin-4-yl}α,α-dimethylphenoxyacetic acid,
4-{1-(2,4-difluorobenzoyl)-4-hydroxypiperidin-4-yl}α,α-dimethylphenoxyacetic acid,
Isopropyl 3-{1-(2,4-difluorobenzoyl)-4-hydroxypiperidin-4-yl}α,α-dimethylphenoxyacetate.

The arylamide derivatives of the formula (1) according to the present invention are prepared, for example, by the following reaction schemes 1 to 5:

Reaction Scheme 1:

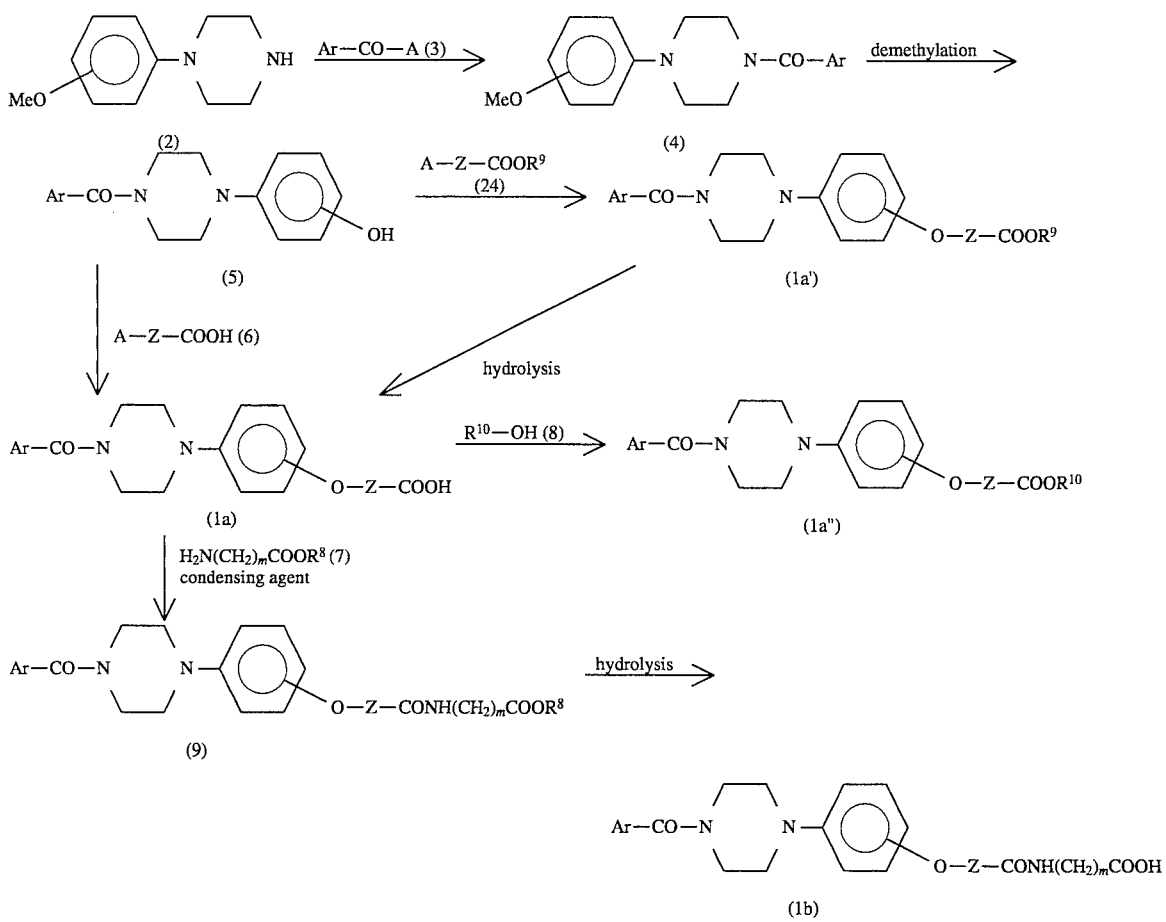

wherein A represents a halogen atom R$^8$, R$^9$ and R$^{10}$ each independently represents an alkyl group, and Ar, Z and m have the same meaning as defined hereinbefore.

In other words, 1-arylpiperazine derivative (2) is reacted with arylcarbonyl halide (3) to obtain a compound (4). Compound (4) is then demethylated to obtain a compound (5). Compound (5) thus obtained is reacted with carboxylic acid (6) to obtain arylamide derivative (1a) of the present invention. Similarly, reaction between compound (5) and compound (24) followed by hydrolysis will also yield arylamide derivative (1a) of the present invention. When the thus obtained compound (1a) is further reacted with an amino acid derivative (7), a compound (9) is obtained, and a hydrolysis of compound (9) yields arylamide derivative (1b) of the present invention. Meanwhile, when compound (1a) is reacted with alcohol (8), arylamide derivative (1a") of the present invention is obtained.

Now, each reaction step will be described in detail.

The reaction between 1-arylpiperazine derivative (2) and arylcarbonyl halide (3) is preferably carried out in a solvent which does not affect the reaction, such as tetrahydrofuran, benzene, toluene, ether, chloroform, methylene chloride and the like in the presence of a base such as triethylamine, pyridine and the like in the temperature range of 0° C. to room temperature. Demethylation of compound (4) is carried out by reacting it with ethanethiol/anhydrous aluminum chloride, boron trichloride or boron tribromide in a solvent which does not affect the reaction, such as methylene chloride, chloroform and the like in the temperature range of 0° C. to room temperature, or by melting with heat together with a pyridinium salt such as pyridine hydrochloride in the temperature range of 130° to 200° C.

The reaction between compound (5) and carboxylic acid (6) and the reaction between compound (5) and compound (24) are generally performed in the presence of a base such as sodium hydroxide, potassium hydroxide, sodium carbonate, potassium carbonate, sodium hydride and the like in the temperature range of 0° to 100° C.

The reaction between compound (1a) and compound (7) is preferably carried out in a solvent which does not affect the reaction, such as methylene chloride, chloroform, tetrahydrofuran, benzene, toluene, ether, and the like in the presence of a base such as triethylamine, pyridine and the like in the temperature range of 0° C. to room temperature.

The hydrolysis of compound (9) and compound (1a') is generally performed in the presence of a base such as potassium hydroxide, sodium hydroxide and the like in a solvent such as water, dioxane, alcohol and the mixture thereof at room temperature.

The reaction between compound (1a) and alcohol (8) is an ordinary esterification reaction carried out in the presence of a catalytic amount of concentrated sulfuric acid, methanesulfonic acid, p-toluenesulfonic acid and the like.

Reaction Scheme 2:

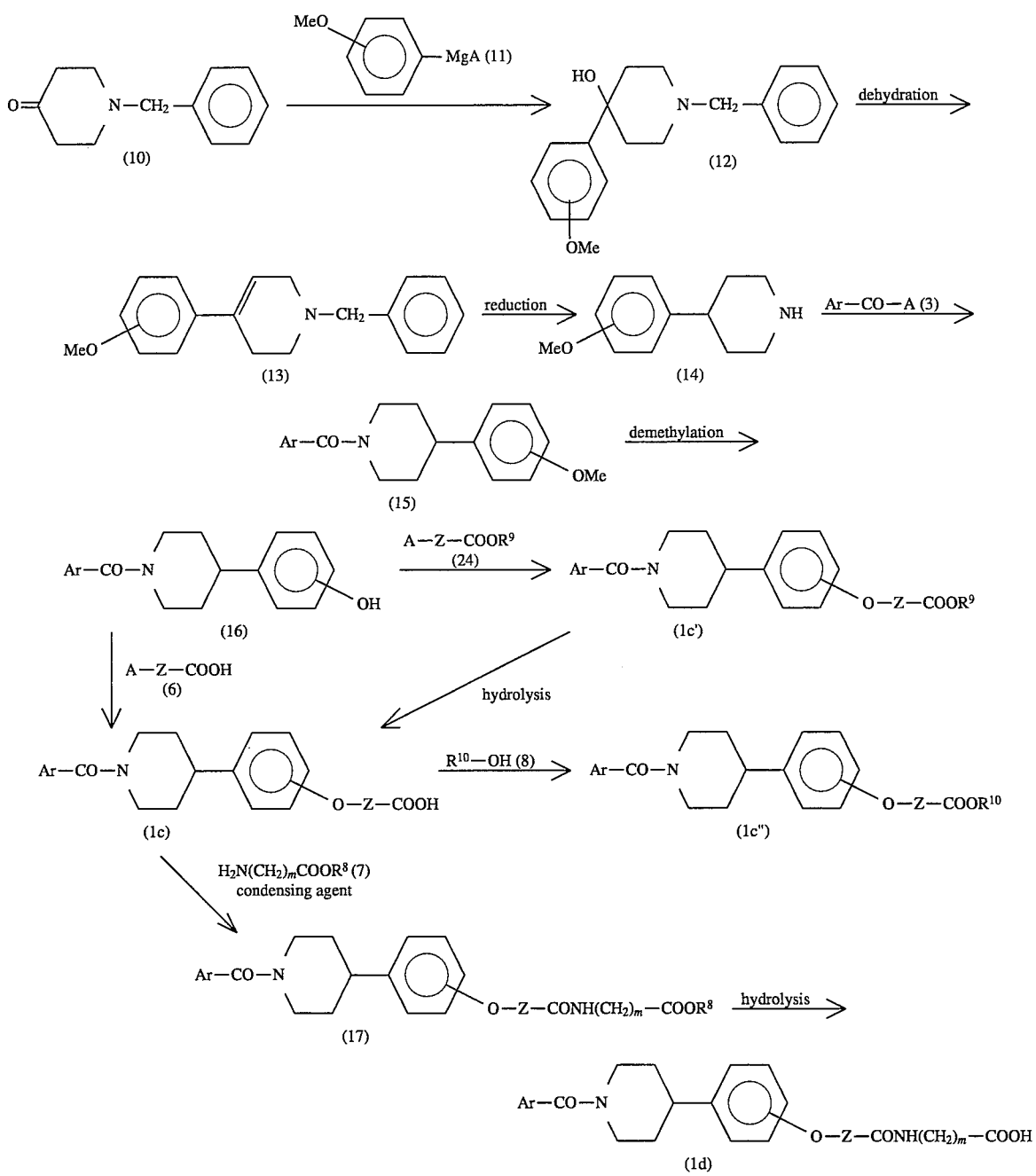

wherein Ar, A, Z, $R^8$, $R^9$ and $R^{10}$ and m have the same meaning as defined hereinbefore.

In other words, 1-benzyl-4-piperidone (10) is reacted with arylmagnesium halide (11) to obtain a compound (12). Compound (12) is then dehydrated to obtain a compound (13). Compound (13) thus obtained is reduced to obtain a 4-arylpiperidine derivative (14). Subsequently, the obtained derivative (14) is reacted with arylcarbonyl halide (3) to obtain a compound (15), followed by demethylation to obtain a compound (16). When compound (16) is reacted with compound (6), arylamide derivative (1c) of the present invention is obtained. Similarly, reaction between compound (16) and compound (24) followed by hydrolysis will also yield arylamide derivative (1c) of the present invention.

When the thus obtained compound (1c) is reacted with an amino acid derivative (7), a compound (17) is obtained, and a hydrolysis of compound (17) yields arylamide derivative (1d) of the present invention.

In the meantime, when compound (1c) is reacted with alcohol (8), arylamide derivative (1c") of the present invention is obtained.

Now, each reaction step will be described in detail.

The reaction between 1-benzyl-4-piperidone (10) and arylmagnesium halide (11) is carried out in a solvent such as tetrahydrofuran, ether and the like under the conditions of an ordinary Grignard's reaction.

Dehydration of compound (12) is performed in a solvent such as benzene, toluene, tetrahydrofuran and the like in the presence of an acid such as sulfuric acid, p-toluenesulfonic acid and methanesulfonic acid while refluxing with heat.

The reduction of compound (13) is an ordinary catalytic hydrogenation using a catalyst such as palladium-on-carbon and palladium hydroxide-on-carbon.

Further, the reaction which introduces compound (1c″) starting from compound (1c) can be performed in a similar manner employed for obtaining compound (1a″) from compound (1a) in Reaction Scheme 1.

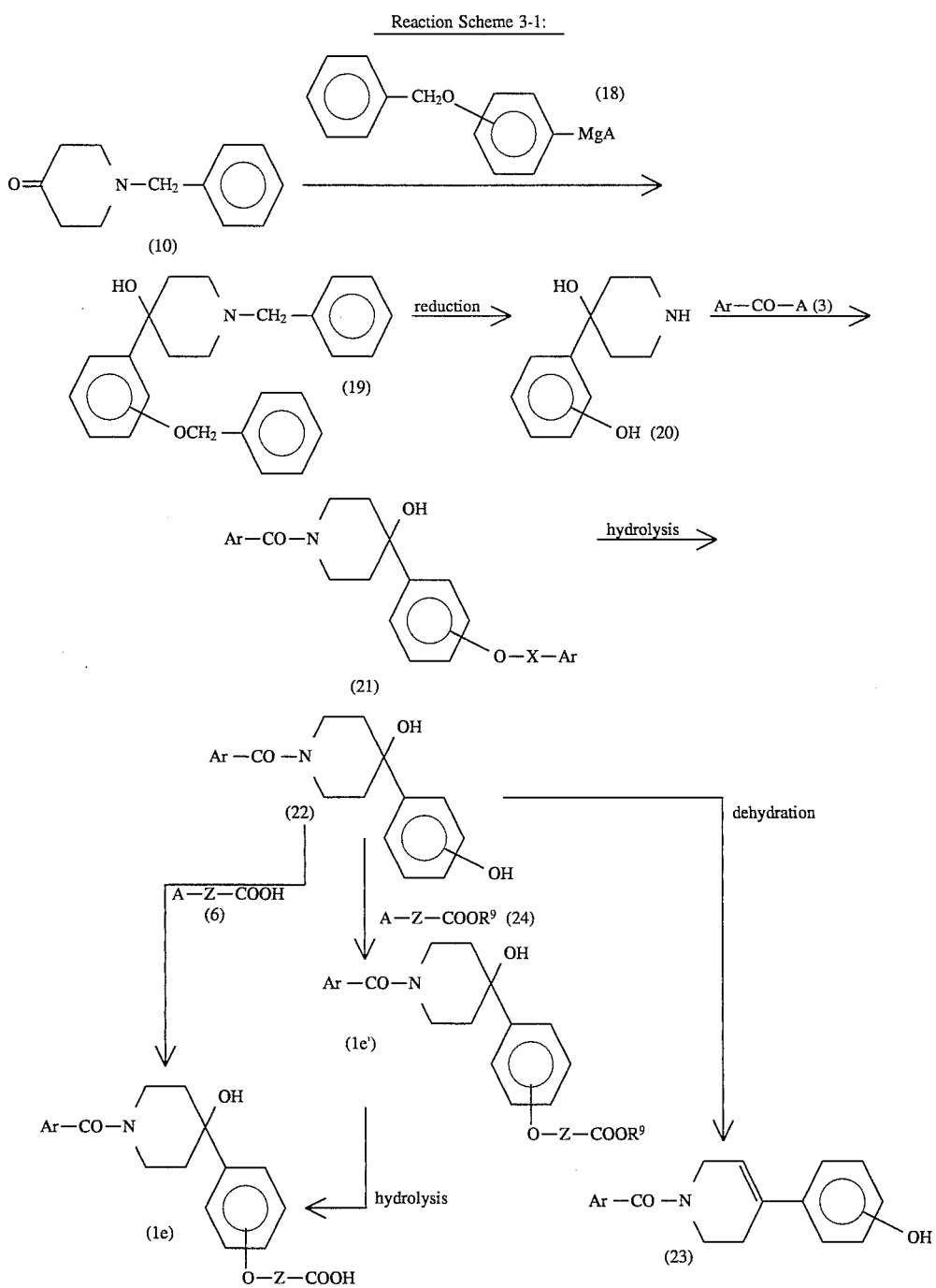

The reaction which introduces arylamide derivative (1c) of the present invention starting from compound (14) can be performed in a similar manner employed for obtaining compound (1a) from compound (2) in Reaction Scheme 1.

The reaction which introduces arylamide derivative (1d) of the present invention starting from compound (1c) can be performed in a similar manner employed in the synthesis of compound (1b) in Reaction Scheme 1.

Reaction Scheme 3-2:

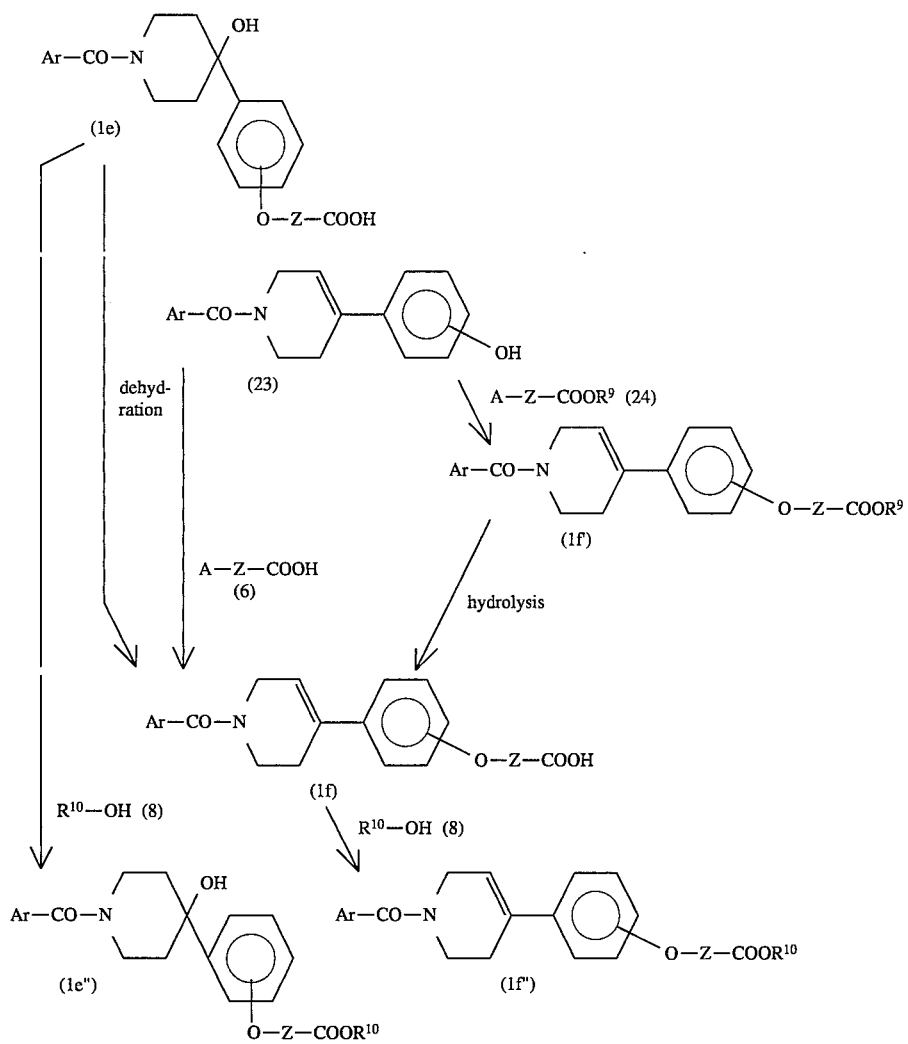

wherein Ar, A, Z, $R^9$, $R^{10}$ and m have the same meaning as defined hereinbefore.

In other words, 1-benzyl-4-piperidone (10) is reacted with arylmagnesium halide (18) to obtain a compound (19). Compound (19) is then reduced to obtain a compound (20). Compound (20) thus obtained is reacted with arylcarbonylhalide (3) to obtain a compound (21), then hydrolyzed to obtain a compound (22).

Subsequently, the obtained compound (22) is reacted with compound (6) to obtain arylamide derivative (1e) of the present invention. Similarly, reaction between compound (22) and compound (24) followed by hydrolysis also yield arylamide derivative (1e) of the present invention.

When compound (22) is dehydrated and the obtained compound (23) is reacted with compound (6), arylamide derivative (1f) of the present invention is obtained. Similarly, reaction between compound (23) and compound (24) followed by hydrolysis also yields arylamide derivative (1f) of the present invention.

When compounds (1e) and (1f) are reacted with alcohol (8), arylamide derivatives (1e") and (1f") of the present invention are obtained, respectively.

In order to prepare compound (19) by the reaction of 1-benzyl-4-piperidone (10) and arylmagnesium halide (18), a similar method for obtaining compound (12) from compound (10) in Reaction Scheme 2 can be followed. The reduction of compound (19) into compound (20) can be performed in a similar manner for obtaining compound (14) from compound (13) in Reaction Scheme 2.

The reaction which introduces compound (21) from compound (20) can be performed in a similar manner for obtaining compound (4) from compound (2) in Reaction Scheme 1. The hydrolysis of compounds (21), (1e') and (1f') can be performed in a similar manner for obtaining compound (1b) from compound (9) described in Reaction Scheme 1. Furthermore, the reactions from compound (22) to compounds (1e) and (1e') can be performed in a similar manner for obtaining compound (1a) from compound (5) described in Reaction Scheme 1. The dehydration of compound (22) into compound (23) is performed in a manner similar to the synthesis of compound (13) from compound (12) described in Reaction Scheme 2. The reaction which introduces compound (1f) from compound (23) is performed in a manner similar to the synthesis of compound (1a) from compound (5) as described in Reaction Scheme 1.

It is also possible to obtain compound (1f) from arylamide derivative (1e). This reaction can be performed in a manner similar to the synthesis of compound (13) from compound (12) as described in Reaction Scheme 2. Further, the reactions which introduce compound (1e") from compound (1e)

and compound (1f") from compound (1f) can be performed in a manner similar to the synthesis of compound (1a") from compound (1a) described in Reaction Scheme 1.

Reaction Scheme 4:

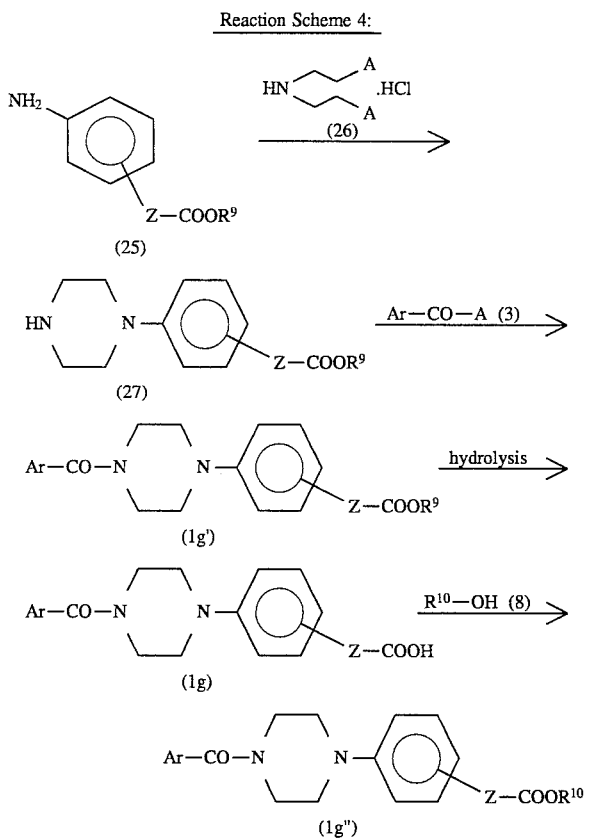

wherein Ar, A, Z, $R^9$ and $R^{10}$ have the same meaning as defined hereinbefore.

In other words, arylaminocarboxylic acid derivative (25) is reacted with bis(2-haloethyl)amine hydrochloride (26) to obtain a compound (27), to which arylcarbonyl halide (3) is reacted to obtain a compound (1g'). Subsequently, the obtained compound (1g') is hydrolyzed to obtain arylamide derivative (1g) of the present invention. When compound (1g) is reacted with alcohol (8), arylamide derivative (1g") of the present invention is obtained.

Now, each reaction step will be described in detail.

The reaction between arylaminocarboxylic acid derivative (25) and bis(2-haloethyl)amine hydrochloride (26) is carried out in a solvent which does not affect the reaction, such as tetrahydrofuran, benzene, toluene, ethanol, methanol and the like while refluxing with heat in the presence of a base such as triethylamine, pyridine and the like.

The reaction for obtaining a compound (1g') from compound (27) can be performed in a similar manner for obtaining compound (4) from compound (2) described in Reaction Scheme 1, and the hydrolysis of compound (1g') can be performed in a similar manner for obtaining compound (1b) from compound (9) described in Reaction Scheme 1.

The reaction for obtaining compound (1g") from compound (1g) can be performed in a similar manner for obtaining compound (1a") from compound (1a) described in Reaction Scheme 1.

Reaction Scheme 5:

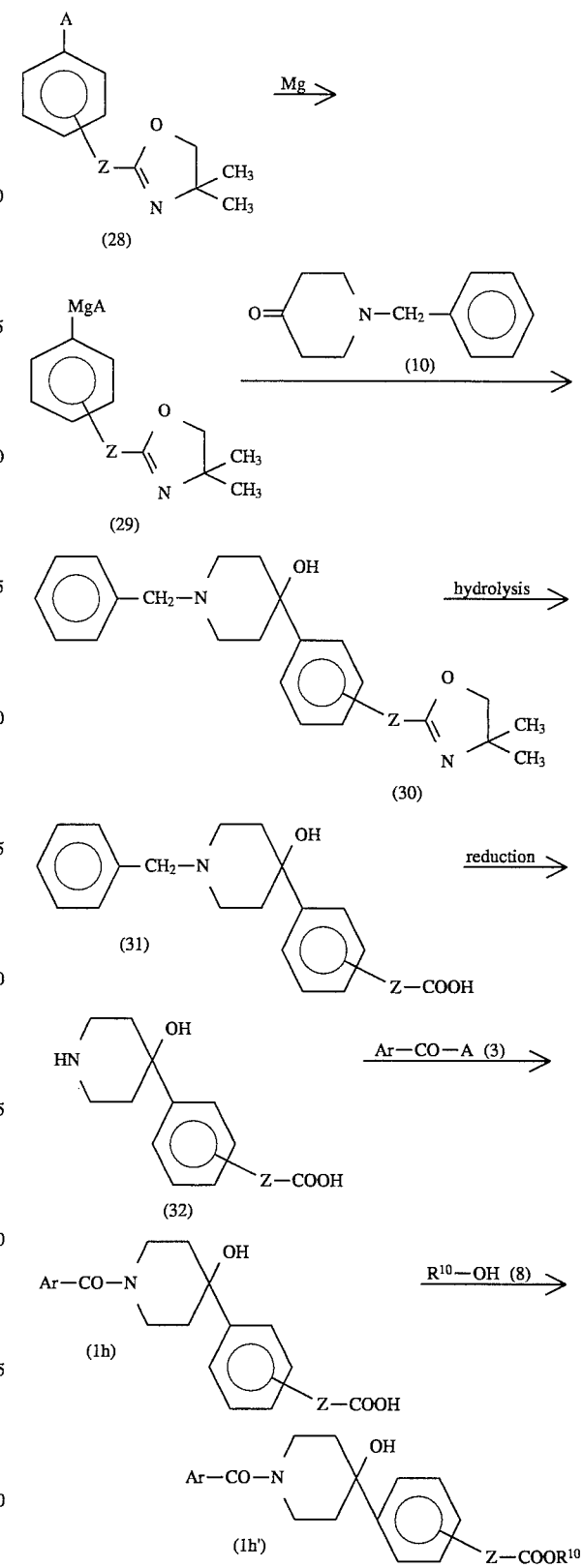

wherein Ar, A, Z and $R^{10}$ have the same meaning as defined hereinbefore.

In other words, arylhalogeno derivative (28) is reacted with Mg to obtain a Grignard's reagent (29), which is further reacted with 1-benzyl-4-piperidone (10) to obtain a compound (30). Subsequently, compound (30) is hydrolyzed to convert into compound (31), then reduced to obtain a compound (32). The thus obtained compound (32) is reacted with arylcarbonyl halide (3) to obtain arylamide derivative (1h) of the present invention. When compound (1h) is reacted with alcohol (8), arylamide derivative (1h') of the present invention can be obtained.

Now, each reaction step will be described in detail.

Grignard's reagent (29) can be prepared by refluxing arylhalogeno derivative (28) together with Mg with heat in a solvent which does not affect the reaction such as ether, tetrahydrofuran and the like, in the presence of a catalytic amount of $I_2$. The reaction between compound (10) and Grignard's reagent (29) can be performed in a similar manner for obtaining compound (12) from compound (10) described in Reaction Scheme 2.

The hydrolysis of compound (30) is an ordinary acid hydrolysis, and performed, for example, by refluxing with heat in ethanol along with diluted hydrochloric acid.

The reduction of compound (31) is performed by adding hydrogen using palladium hydroxide-on-carbon as a catalyst.

The reaction for introducing arylamide derivative (1h) of the present invention from compound (32) can be performed in a similar manner for obtaining compound (4) from compound (2) described in Reaction Scheme 1. The reaction for obtaining (1h') from compound (1h) can be performed in a similar manner for obtaining compound (1a") from compound (1a) described in Reaction Scheme 1.

The arylamide derivative (1) according to the present invention thus obtained can be purified by conventional methods such as extraction using a solvent, recrystallization, column chromatography and the like.

The anti-hyperlipemic action of arylamide derivatives (1) of the present invention will now be described.

(1) Action on serum lipids of healthy mouse:

Groups of 7 week old male ddY mice, each group consisting of 5 mice, were provided for the test. Compounds to be tested were suspended in a 0.5% CMC-Na solution, respectively, and orally administered once a day for three days in total. Twenty-four hours from the last administration, blood was collected by excising the neck of the mice. The collected blood was centrifuged for 10 minutes at 3,000 rpm for collecting serum. The quantities of total cholesterol (T-CHO), β-lipoprotein (β-LP) and triglyceride (TG) in the serum were measured with an automatic analyzer manufactured by Hitachi Co. (Type 7050 Autoanalyzer) and compared with the data of the control group. The results are shown in Table 1.

TABLE 1

| Compound Number | Amount of dosage (mg/kg) | T-CHO (mg/dl) | β-LP (mg/dl) | TG (mg/dl) |
| --- | --- | --- | --- | --- |
| Compound (1) of present invention | 9 | 0.3 | $166^+18$ | $230^+28$ | $201^+23$ |
| | | 1 | $158^+14$ | $201^+16$ | $186^+13$ |
| | | 3 | $174^+12$ | $119+14$ | $115^+10$ |
| | 12 | 100 | $184^+18$ | $96^+19$ | $109^+14$ |
| | 13 | 100 | $168^+16$ | $120^+22$ | $123^+20$ |
| | 24 | 0.3 | $180^+13$ | $211^+23$ | $193^+26$ |
| | | 1 | $164^+14$ | $161^+18$ | $151^+14$ |
| | | 3 | $153^+12$ | $94^+11$ | $101^+9$ |
| | 25 | 0.3 | $151^+9$ | $173^+17$ | $153^+20$ |
| | | 1 | $145^+14$ | $139^+18$ | $136^+14$ |
| | | 3 | $160^+16$ | $95^+14$ | $110+8$ |

TABLE 1-continued

| | Compound Number | Amount of dosage (mg/kg) | T-CHO (mg/dl) | β-LP (mg/dl) | TG (mg/dl) |
| --- | --- | --- | --- | --- | --- |
| Comparative compound | Bezafibrate | 100 | $202^+12$ | $170^+26$ | $148^+25$ |
| Control | | | $198^+9$ | $273^+33$ | $228^+31$ |

(2) Action on rat hyperlipemia induced by Triton WR-1339:

Groups of rats, each group consisting of 5 rats, were fasted overnight, and the compounds to be tested were orally administered to them. Three hours thereafter, 200 mg/kg of Triton WR-1339 was intravenously administered to them. Twenty hours after the administration of Triton WR-1339, blood was collected from the lower aorta under etherization, and centrifuged for 10 minutes at 3,000 rpm for collecting serum. The quantities of total cholesterol (T-CHO), β-lipoprotein (β-LP) and triglyceride (TG) in the serum were measured with an automatic analyzer manufactured by Hitachi Co. (Type 7050 Autoanalyzer) and compared with the data of the control group. The results are shown in Table 2.

TABLE 2

| Test compounds | Amount of dosage (mg/kg) | T-CHO (mg/dl) | β-LP (mg/dl) | TG (mg/dl) |
| --- | --- | --- | --- | --- |
| Compound (1) of the present invention: Compound No. 9 | 1 | $265^+27$ | $718^+108$ | $1654^+305$ |
| | 3 | $249^+26$ | $661^+89$ | $1601+261$ |
| | 10 | $182^+18$ | $372^+112$ | $714^+201$ |
| Comparative compound: Bezafibrate | 10 | $283^+18$ | $731^+157$ | $1676^+273$ |
| | 30 | $245^+20$ | $501^+84$ | $1252^+226$ |
| | 100 | $217^+46$ | $347^+126$ | $1101^+385$ |
| Control | | $330^+18$ | $850^+197$ | $2338^+248$ |

As described above, the arylamide derivative (1) according to the present invention significantly lowered the levels of total cholesterol (T-CHO), β-lipoprotein (β-LP) and triglyceride (TG) in blood compared to the levels achieved by the comparative compound and the control.

Moreover, safety of the arylamide derivative (1) of the present invention was proved by the fact that oral administration in the amount of 300 mg/kg induced no death of mice.

When arylamide derivatives (1) or salts thereof according to the present invention are used as a therapeutic agent for hyperlipemia, the amount of administration differs depending on the body weight, age, sex, general body condition or the condition of the disease of the patient in need thereof and also on the manner of administration, and is suitably from 1 to 200 mg per day in the case of oral administration, and from 0.1 to 20 mg per day in the case of parenteral administration.

The arylamide derivatives (1) according to the present invention can be prepared into various medicinal forms such as tablets, granules, hard capsules, soft capsules, powders, fine-grain pills, pills, suspensions, injections, suppositories, drips, syrups and the like by methods known per se.

In order to prepare solid preparations, the arylamide derivatives (1) according to the present invention are preferably added with vehicles, and if necessary, with binders, disintegrants, lubricants, colorants, flavoring and taste modifying agents, bulking agents, coating agent, sugar coating agents and the like, and then formed into tablets, granules, powders, capsules, suppositories and the like by methods known per se. In order to prepare injections, the arylamide derivatives (1) according to the present invention are dissolved, dispersed or emulsified in an aqueous carrier such as distilled water for injection use in advance, or first prepared into powder suited for injection use and dissolved upon use. Examples of manners of administration of the injections include intravenous, intraportal, intraperitoneal, intramuscular, subcutaneous and the like.

The arylamide derivatives (1) according to the present invention exhibit excellent action of lowering the level of total cholesterol and triglyceride in blood. Since the derivatives are very safe compounds, they are useful for the treatment and prevention of hyperlipemia which is associated with arteriosclerosis, myocardial infarction, hypertension and cerebrovascular disorders.

EXAMPLES

The present invention is now described by way of examples, which however, should not be construed as limiting the present invention thereto.

Example 1

[3-{4-(4-bromobenzoyl)piperazinyl}phenoxy]α,α-dimethylacetic acid (Compound No. 3)

1.90 g (4.00 mmol) of ethyl [3-{4-(4-bromobenzoyl)piperazinyl}phenoxy]α,α-dimethylacetate was dissolved in a solvent mixture containing 20 ml of dioxane and 20 ml of methanol, to which 20 ml of aqueous 1N NaOH solution was added and stirred for 2 hours at room temperature. After completion of the reaction, diluted hydrochloric acid was added to the reaction mixture to convert the system to acidic, followed by extraction with chloroform, washing with water and drying over anhydrous sodium sulfate. Subsequently, chloroform was distilled off under reduced pressure. The oily residue obtained was crystallized from a solvent mixture of petroleum ether, ether and ethyl acetate to obtain 1.45 g (81.0%) of the target compound as colorless crystals.

Example 2

3-{1-(4-bromobenzoyl)piperidin-3-en-4-yl}α,α-dimethylphenoxyacetic acid (Compound No. 5)

1.70 g (3.68 mmol) of 3-{1-(4-bromobenzoyl)-4-hydroxypiperidin- 4-yl}α,α-dimethylphenoxyacetic acid was dissolved in 80 ml of anhydrous tetrahydrofuran, to which 0.50 ml of concentrated sulfuric acid was added and refluxed for 14 hours. The reaction mixture was washed with a saturated saline solution, dried over anhydrous sodium sulfate, and then tetrahydrofuran was distilled off under reduced pressure. The residue was purified by silica gel column chromatography and the eluate of 10% methanol/chloroform was distilled off under reduced pressure, followed by crystallization with ether, to obtain 771 mg (47.0%) of the target compound in crystals.

Example 3

Isopropyl 3-{1-(4-bromobenzoyl)piperidin-3-en-1-yl}!!!!dimethylphenoxyacetate (Compound No. 6)

1.50 g (3.25 mmol) of 3-{1-(4-bromozenzoyl)-4-hydroxypiperidin- 4-yl}!!!!dimethylphenoxyacetic acid was added to 100 ml of isopropyl alcohol, to which 0.10 ml of concentrated sulfuric acid was added and stirred for 54 hours while refluxing. Subsequently, the reaction mixture was addded to a saturated saline solution, extracted with ethyl acetate and dried over anhydrous sodium sulfate. Ethyl acetate was distilled off under reduced pressure and the residue was purified by silica gel column chromatography. The eluate of chloroform was distilled off under reduced pressure to obtain 720 mg (45.6%) of the target compound as an oily material.

Example 4

3-{1-(4-Bromobenzoyl)piperidin-4-yl}!!!!dimethylphenoxy acetic acid (Compound No. 9)

4.20 g (11.0 mmol) of ethyl 3-{1-(4-bromobenzoyl)piperidin- 4-yl}!!!!dimethylphenoxy acetate was dissolved in a solvent mixture containing 25 ml of dioxane and 25 ml of methanol, to which 20 ml of aqueous 2N NaOH solution was added and stirred for 16 hours at room temperature. After completion of the reaction, diluted hydrochloric acid was added to the reaction mixture to convert the system to acidic, followed by extraction with chloroform. Subsequently, the extract was washed with water and dried over anhydrous sodium sulfate, and then chloroform was distilled off under reduced pressure. The oily residue obtained was crystallized from a solvent mixture of petroleum ether and ethyl acetate to obtain 3.73 g (95.8%) of the target compound.

Example 5

3-{1-(4-Bromobenzoyl)-4-hydroxypiperidin-4-yl}α,α-dimethylphenoxy acetic acid (Compound No. 13)

801 mg of {1-(4-bromobenzoyl)-4-(2-hydroxyphenyl)-4-hydroxypiperidine was stirred for 9 hours at the ambient temperature of 100° C. in the presence of 1.20 g (8.68 mmol) of potassium carbonate in 4.00 g (20.5 ml) of ethyl α-bromoisobutyrate. After completion of the reaction, The reaction mixture was cooled, and water was added thereto, followed by extraction with chloroform. Subsequently, the extract was dried over anhydrous sodium sulfate. Chloroform and the remained ethyl α-bromoisobutyrate was distilled off under reduced pressure to obtain 902 mg (86.4%) of ethyl 3 -{1-(4-bromobenzoyl)-4-hydroxypiperidin-4-yl}α,α-dimethylphenoxyacetate.

78 mg of the thus obtained ethyl 3-{1-(4-bromobenzoyl)-4-hydroxypiperidin-4-yl}α,α-dimethylphenoxy acetate was dissolved in a solvent mixture containing 5.0 ml of methanol and 5.0 ml of dioxane, to which 5.0 ml of aqueous 1N NaOH solution was added and stirred for 1 hour at room temperature. After completion of the reaction, diluted hydrochloric acid was added to the reaction mixture to convert the system to acidic, extracted with chloroform, and dried over anhydrous sodium sulfate. Subsequently, chloroform was distilled off under reduced pressure, and then the obtained crystals were pulverized with a solvent mixture of ether and petroleum ether to obtain 63 mg (85%) of 3-{1-(4-bromobenzoyl)-4-hydroxypiperidin-4-yl}α,α-dimethylphenoxy acetic acid in colorless crystals.

The thus obtained compounds in Examples 1 to 5 along with their chemical properties are shown in Tables 3 to 10.

TABLE 3

| | In Formula (1) Y—⌬—(Ar) | | | | | |
|---|---|---|---|---|---|---|
| Compound Nos. | Ar | Q—Z | R⁴ | NMR δ ppm (CDCl₃) | IR (cm⁻¹) | Properties (mp, °C.) |
| 1 | 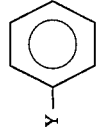 | 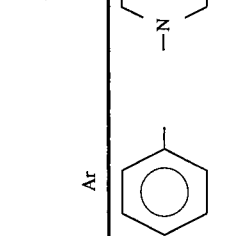 | OH | 1.59(s, 6H), 3.20(br. d, 4H), 3.62(br, 2H), 3.92(br, 2H), 6.48(d, 1H), 6.56(s, 1H), 6.67(d, 1H), 7.16(t, 1H), 7.43(s, 5H). | 1726 1586 (KBr) | Colorless crystals 118–119 |
| 2 | 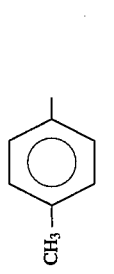 | " | " | 1.59(s, 6H), 2.39(s, 3H), 3.18(br, 4H), 3.66(br, 2H), 3.92(br, 2H), 6.50(d, 1H), 6.61(s, 1H), 6.70(d, 1H), 7.16(t, 1H), 7.22(d, 2H), 7.33(d, 2H). | 1720 1587 (KBr) | Colorless crystals 119–120 |
| 3 |  | " | " | 1.60(s, 6H), 3.18(m, 4H), 3.60(br, 2H), 3.90(br, 2H), 6.47(dd, 1H), 6.56(s, 1H), 6.66(dd, 1H), 7.16(t, 1H), 7.31(d, 2H), 7.57(d, 2H). | 1727 1591 (KBr) | Colorless crystals 112–113 |
| 4 |  | 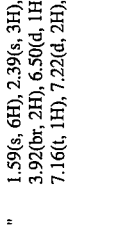 | " | 1.54(s, 7H), 2.52(br. s, 1H), 2.62(br, 1H), 3.55(br. s, 1H), 3.97(br. d, 1H), 4.34(br. s, 1H), 5.70(br. d, 1H), 6.82(d, 1H), 7.00(m, 1H), 7.15(m, 2H), 7.34(d, 2H), 7.55(d, 2H). | 1735 1590 (KBr) | Colorless crystals 164–166 |
| 5 | " | 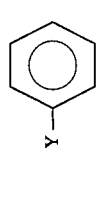 | " | 1.51(s, 6H), 2.50(br. s, 1H), 2.58(br, 1H), 2.69(s, 1H), 3.58(br. s, 1H), 3.98(br. d, 1H), 4.32(br. s, 1H), 6.00(br. d, 1H), 6.83(d, 1H), 6.98(m, 2H), 7.16(t, 1H), 7.34(d, 2H), 7.57(d, 2H). | 1620 1594 (KBr) | Colorless crystals 254 (decomp.) |

TABLE 4

In formula (1)

Y—[phenyl]

| Compound Nos. | Ar | Q—Z | $R^4$ | NMR δ ppm (CDCl$_3$) | IR (cm$^{-1}$) | properties (mp, °C.) |
|---|---|---|---|---|---|---|
| 6 | 4-Br-phenyl | 3-CH$_3$-phenyl-tetrahydropyridine (—N=) | —O—CH(CH$_3$)$_2$ (isopropyl ester via —O—C(CH$_3$)$_2$— shown) | 0.94(d, 1H), 1.22(d, 6H), 1.60(s, 6H), 2.00(br, 1H), 2.54(br, 1H), 3.52(br, 2H), 4.30(br, 1H), 5.08(m, 1H), 6.00(br, 1H), 6.74(m, 1H), 6.84–7.30(m, 3H), 7.34(d, 2H), 7.60(d, 2H). | 1730, 1635 (Neat) | Colorless Oil |
| 7 | phenyl | 3-CH$_3$-phenyl-piperidine (—N—) | OH | 1.59(s, 6H), 1.63–1.91(m, 5H), 2.89(br, 1H), 3.10(br, 1H), 3.88(br, 1H), 4.86(br, 1H), 6.76(dd, 1H), 6.81(s, 1H), 6.90(d, 1H), 7.20(t, 1H), 7.42(s, 5H). | 1741, 1594 (KBr) | Colorless crystals 122–123 |
| 8 | 4-CH$_3$-phenyl | " | " | 1.59(s, 6H), 1.60–1.86(m, 5H), 2.38(s, 3H), 2.97(br, 2H), 3.97(br, 1H), 4.80(br, 1H), 6.76(dd, 1H), 6.81(s, 1H), 6.89(d, 1H), 7.19(t, 1H), 7.21(d, 2H), 7.33(d, 2H). | 3421, 1718, 1578 (KBr) | Colorless crystals 124–125 |
| 9 | 4-Br-phenyl | " | " | 1.59(s, 6H), 1.60–1.91(m, 5H), 2.85(br, 1H), 3.10(br, 1H), 3.83(br, 1H), 4.83(br, 1H), 6.74(dd, 1H), 6.80(s, 1H), 6.88(d, 1H), 7.19(t, 1H), 7.31(d, 2H), 7.54(d, 2H). | 1736, 1587 (KBr) | Colorless crystals 153–154 |
| 10 | 4-Cl-phenyl | 3-CH$_3$-phenyl-4-OH-piperidine (—N—) | —O—CH(H)— (formate) | 1.65–2.15(m, 4H), 3.20–3.70(m, 4H), 3.80(br, 1H), 4.60(br, 1H), 4.64(s, 2H), 6.80(dd, 1H), 7.07(d, 1H), 7.08(d, 1H), 7.27(t, 1H), 7.36(d, 2H), 7.39(d, 2H). | 3400, 1735, 1590 (KBr) | Colorless crystals 164–166 |

TABLE 5

| | In formula (1) | | | | | |
|---|---|---|---|---|---|---|
| Compound Nos. | Ar | Y: phenyl; piperidine-N with 4-OH and 4-(m-tolyl) | Q—Z | R⁴ | NMR δ ppm (CDCl₃) | IR (cm⁻¹) | Properties (mp, °C.) |
| 11 | phenyl | | —O—C(CH₃)₂—CH₃ | OH | 1.52(s, 6H), 1.72(m, 4H), 3.40(m, 4H), 4.20(br, 1H), 6.68(dt, 1H), 7.12(m, 3H), 7.40(s, 5H). | 3200, 1740, 1595 (KBr) | Colorless crystals 162–163 |
| 12 | 4-Cl-phenyl | | " | " | 1.60(s, 6H), 1.55–2.20(m, 4H), 3.15–3.75(m, 4H), 3.80(br, 1H), 4.57(br, 1H), 6.81(dd, 1H), 7.07(d, 1H), 7.10(br. d, 1H), 7.23(t, 1H), 7.36(d, 2H), 7.39(d, 2H). | 3400, 1720, 1600 (KBr) | Colorless crystals 158–159 |
| 13 | 4-Br-phenyl | | " | " | 1.60(s, 6H), 1.60–2.20(m, 4H), 3.15–3.80(m, 4H), 4.60(br, 1H), 6.82(dd, 1H), 7.07(d, 1H), 7.09(d, 1H), 7.26(t, 1H), 7.30(d, 2H), 7.54(d, 2H). | 3510, 1720, 1590 (KBr) | Colorless crystals 170–171 |
| 14 | 4-I-phenyl | | " | " | 1.50(s, 6H), 1.60–2.20(m, 4H), 3.40(br, 4H), 4.30(br, 1H), 6.68(dt, 1H), 6.90–7.24(m, 3H), 7.24(d, 2H), 7.80(d, 2H). | 3420, 1720, 1590 (KBr) | Colorless crystals 154–155 |
| 15 | 4-methylpyridyl | | " | " | 1.49(s, 6H), 1.60(m, 2H), 1.90(m, 2H), 3.10–3.60(br, 4H), 4.43(br, 1H), 6.68(m, 1H), 6.90–7.23(m, 3H), 7.47(m, 1H), 7.87(m, 1H), 8.65(m, 2H). | 3420, 1610 (KBr) | Colorless crystals 113–115 |

TABLE 6

| Compound Nos. | In Formula (I) Ar | [structure] | Q—Z | R⁴ | NMR δ ppm (CDCl₃) | IR (cm⁻¹) | Properties (mp, °C.) |
|---|---|---|---|---|---|---|---|
| 16 | 4-Br-phenyl | 4-hydroxy-4-(4-methylphenyl)piperidine | $\begin{array}{c}CH_3\\|\\-O-C-\\|\\CH_3\end{array}$ | OH | 1.59(s, 6H), 1.73(m, 1H), 1.88(m, 2H), 2.08(m, 1H), 2.50(br, 2H), 3.33(m, 1H), 3.58(br, 2H), 4.57(m, 1H), 6.88(d, 2H), 7.30(d, 2H), 7.34(d, 2H), 7.56(d, 2H). | 3400, 1740, 1600 (KBr) | Colorless crystals 127–128 |
| 17 | " | 4-hydroxy-4-(2-methylphenyl)piperidine | " | " | 1.45(m, 2H), 1.59(s, 6H), 2.55(br, 2H), 3.20(br, 1H), 3.50(br, 2H), 4.40(br, 1H), 4.52(br, 1H), 6.60(d, 1H), 6.92(t, 1H), 7.13(m, 1H), 7.34(d, 2H), 7.63(dd, 1H), 7.67(d, 2H). | 3540, 1720, 1580 (KBr) | Colorless crystals 207–208 |
| 18 | " | 4-hydroxy-4-(3-methylphenyl)piperidine | " | $\begin{array}{c}CH_3\\|\\-O-CH\\|\\CH_3\end{array}$ | 1.20(d, 6H), 1.60(s, 6H), 1.80(br, 4H), 1.90(s, 1H), 3.46(br, 3H), 4.50(br, 1H), 5.16(m, 1H), 6.70(m, 1H), 7.06(m, 3H), 7.30(d, 2H), 7.58(d, 2H). | 3400, 1730, 1620 (Neat) | Colorless oil |
| 19 | 3-methylpyridyl | " | " | OH | 1.54(s, 6H), 0.80–2.00(m, 5H), 3.48(br, 3H), 4.50(br, 1H), 6.76(d, 1H), 7.00–7.48(m, 5H), 7.82(d, 1H), 8.60(br, 1H). | 3421, 1718, 1617 (KBr) | Colorless crystals 113–115 |
| 20 | 3,5-diiodo-4-methylphenyl | " | " | " | 1.60(s, 6H), 0.80–2.00(m, 6H), 3.00–3.72(br, 2H), 4.32–4.60(br, 1H), 6.74–7.44(m, 4H), 7.86(s, 2H). | 3421, 1719, 1605 (KBr) | Colorless crystals 125–127 |

TABLE 7

In Formula (I)

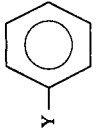

| Compound Nos. | Ar | Q—Z | R⁴ | NMR δ ppm (CDCl₃) | IR (cm⁻¹) | Properties (mp, °C.) |
|---|---|---|---|---|---|---|
| 21 | 4-nitrophenyl with tetrahydropyran | $-O-C(CH_3)_2-CH_3$ (—O—C(CH₃)₂ with CH₃) | OH | 1.44(s, 6H), 1.55(d, 1H), 1.72(d, 1H), 1.86–1.91(m, 2H), 3.17(t, 1H), 3.29(d, 1H), 3.46(t, 1H), 4.40(d, 1H), 6.74(dd, 1H), 7.01–7.03(m, 2H), 7.11(t, 1H), 7.43(dd, 2H), 8.65(dd, 2H). | 3404 1617 (KBr) | Colorless crystals 180–182 |
| 22 | 4-F-phenyl with 4-(OH)-piperidine-phenyl | " | " | 1.58(s, 6H), 1.62–1.83(m, 3H), 2.02(br, 1H), 3.22(br, 1H), 3.52(br, 2H), 4.29(br, 2H), 4.58(br, 1H), 6.77–6.80(m, 1H), 7.06–7.10(m, 4H), 7.19–7.23(m, 1H), 7.39–7.43(m, 2H). | 3422, 1734, 1605 (KBr) | Colorless crystals 77–79 |
| 23 | 3,5-di-t-Bu-4-OH-phenyl | " | " | 1.39(s, 18H), 1.43(s, 6H), 1.64(m, 2H), 1.84(m, 2H), 3.28(br, 3H), 4.00(br, 1H), 5.00(br, 1H), 6.75(dd, 1H), 6.96(d, 1H), 6.97(s, 1H), 7.09(t, 1H), 7.18(s, 2H), 7.24(br, 1H). | 3404 1601 (KBr) | Colorless crystals 223–225 |
| 24 | 4-Cl-phenyl with 4-piperidine-phenyl | " | " | 1.50(s, 6H), 1.57(m, 2H), 1.77(br, 2H), 2.76(t, 1H), 2.90(br, 1H), 3.10(br, 1H), 3.63(br, 1H), 4.58(br, 1H), 6.65(dd, 1H), 6.75(d, 1H), 6.88(d, 1H), 7.18(t, 1H), 7.45(d, 2H), 7.50(d, 2H), 12.90(br, 1H). | 1734 1597 (KBr) | Colorless crystals 140–141 |
| 25 | 4-F-phenyl | " | " | 1.49(s, 6H), 1.58(m, 2H), 1.77(br, 2H), 2.76(m, 1H), 3.00(br, 2H), 3.69(br, 1H), 4.55(br, 1H), 6.65(dd, 1H), 6.75(t, 1H), 6.88(d, 1H), 7.18(t, 1H), 7.26(m, 2H), 7.49(m, 2H), 12.80(br, 1H). | 1734 1605 (KBr) | Colorless crystals 138–139 |

TABLE 8

| Compound Nos. | In Formula (I) Ar | Q—Z | R⁴ | NMR δ ppm (CDCl₃) | IR (cm⁻¹) | Properties (mp, °C.) |
|---|---|---|---|---|---|---|
| 26 | 3,5-di-tert-butyl-4-hydroxyphenyl | 1-(phenyl)piperidin-4-yl, —O—C(CH₃)₂— | OH | 1.39(s, 18H), 1.42(s, 6H), 1.54(m, 2H), 1.80(m, 2H), 2.70(t, 1H), 2.95(br, 2H), 3.28(br, 1H), 4.20(br, 1H), 6.72(m, 3H), 7.08(t, 1H), 7.17(s, 2H), 7.24(br, 1H). | 3448 1602 (KBr) | Colorless crystals 148–150 |
| 27 | 3-methylpyridin-2-yl | " | " | 1.60(s, 6H), 1.64–2.12(m, 4H), 2.60–3.16(m, 4H), 4.80(br, 1H), 6.60–6.88(m, 3H), 7.10–7.46(m, 2H), 7.80(dt, 1H), 8.70(br, 2H). | 3447, 1718 1610 (KBr) | Colorless crystals 149–150 |
| 28 | 3,5-di-tert-butyl-4-hydroxyphenyl | " | —O—CH(CH₃)₂ | 1.21(d, 6H), 1.45(s, 18H), 1.59(s, 6H), 1.65(m, 2H), 1.88(m, 2H), 2.72(m, 1H), 2.97(br, 2H), 4.18(br, 1H), 4.70(br, 1H), 5.08(m, 1H), 5.39(s, 1H), 6.67(dd, 1H), 6.74(t, 1H), 6.83(d, 1H), 7.17(t, 1H), 7.27(s, 2H). | 3318, 1730 1602 (KBr) | Colorless crystals 140–141 |
| 29 | 4-trifluoromethylphenyl | " | OH | 1.48(s, 6H), 1.58(m, 2H), 1.77(d, 2H), 2.76(t, 1H), 2.88(br, 1H), 3.17(br, 1H), 3.53(br, 1H), 4.61(br, 1H), 6.66(dd, 1H), 6.75(s, 1H), 6.86(d, 1H), 7.16(t, 1H), 7.65(d, 2H), 7.81(d, 2H). | 1721 1595 (KBr) | Colorless crystals 148–149 |
| 30 | 5-methylfuran-2-yl | " | " | 1.60(s, 6H), 1.69–1.76(m, 2H), 1.92(d, 2H), 2.77–2.79(m, 1H), 3.04(br, 2H), 4.67(br, 2H), 6.48(dd, 1H), 6.77(dd, 1H), 6.91(d, 1H), 7.02(d, 1H), 7.20(t, 1H), 7.49(d, 1H). | 1731 1592 (Neat) | Colorless oil |

TABLE 9

In Formula (I): Y = phenyl

| Compound Nos. | Ar | Q—Z | R⁴ | NMR δ ppm (CDCl₃) | IR (cm⁻¹) | Properties (mp, °C.) |
|---|---|---|---|---|---|---|
| 31 | 2-methylthiophene | 4-(3-methylphenyl)piperidin-1-yl, -O-C(CH₃)₂- | OH | 1.69(s, 6H), 1.60–1.72(m, 2H), 1.91(d, 2H), 2.71–2.77(m, 1H), 3.04(br, 2H), 4.58(br, 2H), 6.67(dd, 1H), 6.74(t, 1H), 6.85(d, 1H), 7.05(dd, 1H), 7.17(t, 1H), 7.31(dd, 1H), 7.45(dd, 1H). | 1697, 1580 (Neat) | Colorless oil |
| 32 | 3-methylpyridine | 4-(3-methylphenyl)piperazin-1-yl, " | " | 1.42(s, 6H), 3.00–3.90(m, 8H), 6.34(dd, 1H), 6.44(t, 1H), 6.49(dd, 1H), 7.01(t, 1H), 7.48(m, 1H), 7.86(dt, 1H), 8.65(m, 2H). | 3408, 1599 (KBr) | Colorless crystals 158–160 |
| 33 | 4-methoxyphenyl | " | " | 1.58(s, 6H), 3.15(br, 4H), 3.74(br, 4H), 3.84(s, 3H), 6.44(d, 1H), 6.51(s, 1H), 6.62(br, 1H), 6.92(d, 2H), 7.14(t, 1H), 7.40(d, 2H). | 1720, 1598 (KBr) | Colorless crystals 168–170 |
| 34 | 3,5-di-tert-butyl-4-hydroxyphenyl | " | " | 1.40(s, 18H), 1.46(s, 6H), 3.00–3.70(m, 8H), 6.28(dd, 1H), 6.42(t, 1H), 6.55(dd, 1H), 7.06(t, 1H), 7.18(s, 2H), 7.28(br, 1H). | 3448, 1734, 1600 (KBr) | Colorless crystals 183–185 |
| 35 | " | " | —O—CH(CH₃)₂ (isopropoxy) | 1.22(d, 6H), 1.45(s, 18H), 1.59(s, 6H), 3.18(br, 4H), 3.78(br, 4H), 5.07(m, 1H), 5.43(s, 1H), 6.35(d, 1H), 6.50(s, 1H), 6.60(br, 1H), 7.11(t, 1H), 7.27(s, 2H). | 3517, 1727, 1625 (KBr) | Colorless crystals 134–135 |

TABLE 10

| Compound Nos. | In Formula (I) | | | | NMR δ ppm (CDCl₃) | IR (cm⁻¹) | Properties (mp, °C.) |
|---|---|---|---|---|---|---|---|
| | Ar | Y—⬡ | Q—Z | R⁴ | | | |
| 36 |  |  | —O—C(CH₃)₂— | OH | 1.61(s, 6H), 3.20(t, 4H), 3.89(t, 4H), 6.45(dd, 1H), 6.53(t, 1H), 6.62(dd, 1H), 7.07(dd, 1H), 7.15(t, 1H), 7.34(dd, 1H), 7.48(dd, 1H). | 1731 1599 (Neat) | Colorless oil |

What is claimed is:

1. An arylamide derivative represented by the formula (1) or a salt thereof:

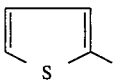   (1)

wherein Ar represents a group

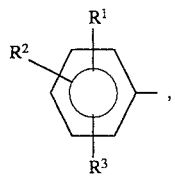

in which $R^1$, $R^2$ and $R^3$ are the same or different from each other and each independently represents a hydrogen atom, a halogen atom, a hydroxyl group, an alkyl group which may be substituted by a halogen atom, an alkoxy group, an alkenyl group, an acylamino group or a carboxyalkyloxy group, a naphthyl group, a pyridinyl group, a furyl group, a thienyl group, a quinolyl group or an indolyl group; Y represents a group

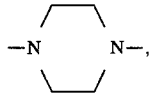

and Q represents —O—, Z represents a C1 to C3 alkylene group or a group

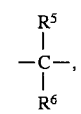

in which $R^5$ and $R^6$ each independently represents an alkyl group; $R^4$ represents a hydroxyl group, an alkoxy group or a group —NH(CH₂)$_m$COOH, in which m is a number of 1 to 3.

2. The compound according to claim 1, wherein Ar represents a group

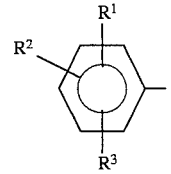

in which $R^1$, $R^2$ and $R^3$ have the same meaning as defined in claim 1, or a pyridinyl group; Y represents a group

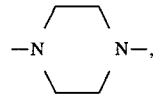

and Q represents —O—, Z represents a group

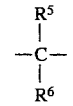

in which $R^5$ and $R^6$ have the same meaning as defined in claim 1; and $R^4$ represents a hydroxyl group or an alkoxy group.

* * * * *

UNITED STATES PATENT AND TRADEMARK OFFICE
CERTIFICATE OF CORRECTION

PATENT NO. : 5,532,371
DATED : JULY 2, 1996
INVENTOR(S) : TERUO KOMOTO, ET AL.

It is certified that error appears in the above-identified patent and that said Letters Patent is hereby corrected as shown below:

On the title page item [54], and column 1, line 3,

"HYPERLIPIMIA"

should read --HYPERLIPEMIA--.

Column 29, line 65, "(4-bromozenzoyl)"

should read --(4-bromobenzoyl)--.

Signed and Sealed this

Thirty-first Day of March, 1998

*Attest:*

BRUCE LEHMAN

*Attesting Officer*     Commissioner of Patents and Trademarks